United States Patent
Mahmoudi

(10) Patent No.: US 11,548,011 B2
(45) Date of Patent: Jan. 10, 2023

(54) MAGNETIC LEVITATION TECHNIQUES TO SEPARATE AND ANALYZE MOLECULAR ENTITIES

(71) Applicant: The Brigham and Women's Hospital, Inc., Boston, MA (US)

(72) Inventor: Morteza Mahmoudi, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/262,644

(22) PCT Filed: Jul. 23, 2019

(86) PCT No.: PCT/US2019/042929
§ 371 (c)(1),
(2) Date: Jan. 22, 2021

(87) PCT Pub. No.: WO2020/023443
PCT Pub. Date: Jan. 30, 2020

(65) Prior Publication Data
US 2021/0260601 A1 Aug. 26, 2021

Related U.S. Application Data

(60) Provisional application No. 62/807,473, filed on Feb. 19, 2019, provisional application No. 62/701,925, filed on Jul. 23, 2018.

(51) Int. Cl.
*B03C 1/32* (2006.01)
*B03C 1/01* (2006.01)
(Continued)

(52) U.S. Cl.
CPC .................. *B03C 1/32* (2013.01); *B03C 1/01* (2013.01); *G01N 33/54346* (2013.01);
(Continued)

(58) Field of Classification Search
CPC ........... B03C 1/32; B03C 1/01; B03C 1/0332; B03C 1/0335; B03C 1/0337; B03C 1/288;
(Continued)

(56) References Cited

U.S. PATENT DOCUMENTS 9,517,474 B2 * 12/2016 Mao .......................... B03C 1/32
9,968,943 B2 * 5/2018 Khashan ................... B03C 1/01
(Continued)

FOREIGN PATENT DOCUMENTS

| EP | 1012593 | | 6/2000 | |
| EP | 1012593 B1 * | | 6/2005 | ....... G01N 27/44721 |
| WO | WO-2020190845 A1 * | | 9/2020 | ............... B03C 1/01 |

OTHER PUBLICATIONS

McCloskey, Magnetic Cell Separation: Characterization of Magnetophoretic Mobility, Dec. 15, 2003 (Year: 2003).*
(Continued)

*Primary Examiner* — Gene O Crawford
*Assistant Examiner* — Muhammad Awais
(74) *Attorney, Agent, or Firm* — Fish & Richardson P.C.

(57) ABSTRACT

The disclosure describes systems and methods for separating a plurality of molecular entities with differing densities. The system includes: a pair of magnetic poles of like polarity to provide a magnetic field; and a container holding the plurality of molecular entities in a fluid medium comprising nanoparticles that substantially change a magnetic susceptibility of the fluid medium such that, when the container is placed inside the magnetic field, sufficient gradients in an effective density of the fluid medium are generated inside the container to levitate the plurality of molecular entities to respective layers within the container, each respective layer corresponding to a respective density.

20 Claims, 21 Drawing Sheets

(51) Int. Cl.
  *G01N 33/543* (2006.01)
  *G01N 33/574* (2006.01)
(52) U.S. Cl.
  CPC ........ *G01N 33/574* (2013.01); *B03C 2201/18* (2013.01); *B03C 2201/26* (2013.01)
(58) Field of Classification Search
  CPC ............ B03C 2201/18; B03C 2201/26; G01N 33/54346; G01N 33/574
  USPC .......................................................... 209/39
  See application file for complete search history.

(56) References Cited

U.S. PATENT DOCUMENTS

| | | | | |
|---|---|---|---|---|
| 10,676,719 | B2* | 6/2020 | Mao ..................... | C12N 5/0693 |
| 2005/0009002 | A1* | 1/2005 | Chen ........................ | B01J 13/12 435/4 |
| 2008/0290037 | A1* | 11/2008 | Liu ........................... | B03C 1/32 210/93 |
| 2009/0047297 | A1* | 2/2009 | Kim ........................ | B03C 1/288 210/695 |
| 2010/0093052 | A1* | 4/2010 | Chalmers ................ | B03C 1/288 435/308.1 |
| 2012/0080360 | A1* | 4/2012 | Stone ........................ | B03C 1/01 210/695 |
| 2012/0164396 | A1* | 6/2012 | Mirkin .................... | C09D 11/03 427/256 |
| 2013/0134041 | A1* | 5/2013 | Tamura ................ | B01L 3/50273 204/547 |
| 2013/0240456 | A1* | 9/2013 | Radisic ..................... | B03C 1/01 210/695 |
| 2015/0153259 | A1* | 6/2015 | Liberti ..................... | G01N 1/04 435/309.1 |
| 2016/0370386 | A1* | 12/2016 | Demirci ............ | B01L 3/502715 |

OTHER PUBLICATIONS

Mahmoudi, Superparamagnetic Iron Oxide Nanoparticles with Rigid Cross-linked Polyethylene Glycol Furmarte Coating for Application in Imaging and drug Delivery, Apr. 16, 2009 (Year: 2009).*
Ashkarran et al., "Evolving magnetically levitated plasma proteins detects opioid use disorder as a model disease," Advanced Healthcare Materials, Mar. 2020, 9(5):1901608.
Ashkarran et al., "Magnetic levitation systems for disease diagnostics," Trends in Biotechnology, Mar. 1, 2021, 39(3):311-21.
Ashkarran et al., "Magnetically levitated plasma proteins," Analytical Chemistry, Jan. 9, 2020, 92(2):1663-8.
Amiri et al., "Protein corona affects the relaxivity and MRI contrast efficiency of magnetic nanoparticles," Nanoscale, Jun. 2013, 5(18):8656-65.
Askim et al., "Optical sensor arrays for chemical sensing: the optoelectronic nose," Chemical Society Reviews, 2013, 42(22):8649-82.
Badieyan et al., "Detection and discrimination of bacterial colonies with Mueller matrix imaging," Scientific Reports, Jul. 17, 2018, 8(1), 10 pages.
Baird et al., "Blood-based proteomic biomarkers of Alzheimer's disease pathology," Frontiers in Neurology, Nov. 16, 2015, 6:236, 16 pages.
Bertrand et al., "Mechanistic understanding of in vivo protein corona formation on polymeric nanoparticles and impact on pharmacokinetics" Nature Communications, Oct. 3, 2017, 8(1):1-8.
Bigdeli et al., "Exploring cellular interactions of liposomes using protein corona fingerprints and physicochemical properties," ACS nano, Mar. 22, 2016, 10(3):3723-37.
Bwambok et al., "Paramagnetic ionic liquids for measurements of density using magnetic levitation," Analytical Chemistry, Sep. 3, 2013, 85(17):8442-7.

Caracciolo et al., "Biological identity of nanoparticles in vivo: clinical implications of the protein corona," Trends in Biotechnology, Mar. 1, 2017, 35(3):257-64.
Carey et al., "Rapid identification of bacteria with a disposable colorimetric sensing array," Journal of the American Chemical Society, May 18, 2011, 133(19):7571-6.
Carter et al., "Early detection of prostate cancer: AUA Guideline," The Journal of Urology, Aug. 2013, 190(2):419-26.
Croft et al., "The Reactome pathway knowledgebase," Nucleic Acids Research, Jan. 1, 2014, 42(D1):D472-7.
Cuzick et al., "Prevention and early detection of prostate cancer," The Lancet Oncology, Oct. 1, 2014, 15(11):e484-92.
Durmus et al., "Magnetic levitation of single cells," Proceedings of the National Academy of Sciences, Jul. 14, 2015, 112(28):E3661-8.
Esteva et al., "Dermatologist-level classification of skin cancer with deep neural networks," Nature, Feb. 2017, 542(7639):115-8.
Etzioni et al., "The case for early detection," Nature Reviews Cancer, Apr. 2003, 3(4):243-52.
Europe PMC Consortium, "Europe PMC: a full-text literature database for the life sciences and platform for innovation," Nucleic Acids Research, Jan. 28, 2015, 43(D1):D1042-8.
Ferrari, "Cancer nanotechnology: opportunities and challenges," Nature Reviews Cancer, Mar. 2005, 5(3):161-71.
Fischer et al., "Average protein density is a molecular-weight-dependent function," Protein Science, Oct. 2004, 13(10):2825-8.
Fontana et al., "Early lung cancer detection: results of the initial (prevalence) radiologic and cytologic screening in the Mayo Clinic study," American Review of Respiratory Disease, Oct. 1984, 130(4):561-5.
Forbes et al., "COSMIC: exploring the world's knowledge of somatic mutations in human cancer," Nucleic Acids Research, Jan. 28, 2015, 43(D1):D805-11.
Ghasemi et al., "Identification of catecholamine neurotransmitters using fluorescence sensor array," Analytica Chimica Acta, Apr. 21, 2016, 917:85-92.
Guo et al., "Alzheimer's Disease Neuroimaging Initiative Plasma proteomics for the identification of Alzheimer's disease," Alzheimer Disease and Associated Disorders, Oct. 2013, 27(4).
Hajipour et al., " Advances in alzheimer's diagnosis and therapy: The implications of nanotechnology," Trends in Biotechnology, Oct. 2017, 35(10):937-53.
Hajipour et al., "Personalized disease-specific protein corona influences the therapeutic impact of graphene oxide," Nanoscale, 2015, 7(19):8978-94.
Hajipour et al., "Personalized protein coronas: a "key" factor at the nanobiointerface," Biomaterials Science, May 2014, 2(9):1210-21.
Hajipour et al., "Sensing of Alzheimer's disease and multiple sclerosis using nano-bio interfaces," Journal of Alzheimer's Disease, Jan. 1, 2017, 59(4):1187-202.
Hanash et al., "Mining the plasma proteome for cancer biomarkers," Nature, Apr. 2008, 452(7187):571-9.
Henschke et al., "Early Lung Cancer Action Project: overall design and findings from baseline screening," The Lancet, Jul. 10. 1999, 354(9173):99-105.
Hirsch et al., "Early detection of lung cancer: clinical perspectives of recent advances in biology and radiology," Clinical Cancer Research, Jan. 1, 2001, 7(1):5-22.
Hirschbein et al., "Magnetic separations in chemistry and biochemistry," Chemtech, Mar. 1982, 12(3):172-9.
Hye et al., "Proteome-based plasma biomarkers for Alzheimer's disease," Brain, Nov. 1, 2006, 129(11):3042-50.
Kantardjieff et al., "Matthews coefficient probabilities: improved estimates for unit cell contents of proteins, DNA, and protein-nucleic acid complex crystals," Protein Science, Sep. 2003, 12(9):1865-71.
Keshishian et al., "Quantitative, multiplexed workflow for deep analysis of human blood plasma and biomarker discovery by mass spectrometry," Nature Protocols, Aug. 2017, 12(8):1683, 39 pages.
Koscielny et al., "Open Targets: a platform for therapeutic target identification and validation," Nucleic Acids Research, Jan. 4, 2017, 45(D1):D985-94.
Kose et al., "Ferrofluid mediated nanocytometry," Lab on a Chip, Oct. 20, 2011, 12(1):190-6.

(56) References Cited

OTHER PUBLICATIONS

Kostic et al., "The dynamics of the human infant gut microbiome in development and in progression toward type 1 diabetes," Cell Host & Microbe, February Feb. 11, 2015:17(2):260-73.
Laurent et al., "Magnetic fluid hyperthermia: focus on superparamagnetic iron oxide nanoparticles," Advances in Colloid and Interface Science, Aug. 10, 2011, 166(1-2):8-23.
Levin et al., "Screening and surveillance for the early detection of colorectal cancer and adenomatous polyps, 2008: a joint guideline from the American Cancer Society, the US Multi-Society Task Force on Colorectal Cancer, and the American College of Radiology," Gastroenterology, May 1, 2008, 134(5):130-60.
Lim et al., "An optoelectronic nose for the detection of toxic gases," Nature Chemistry, Oct. 2009, 1(7):562-7.
Liu et al., "Biomarkers in Alzheimer's disease analysis by mass spectrometry-based proteomics," International Journal of Molecular Sciences, May 2014, 15(5):7865-82.
Lockett et al., "Analyzing forensic evidence based on density with magnetic levitation," Journal of Forensic Sciences, Jan. 2013, 58(1):40, 23 pages.
Mahmoudi et al., "Antibody orientation determines corona mistargeting capability," Nature Nanotechnology, Sep. 2018, 13(9):775-6.
Mahmoudi et al., "Assessing the in vitro and in vivo toxicity of superparamagnetic iron oxide nanoparticles," Chemical Reviews, Apr. 11, 2012, 112(4):2323-38.
Mahmoudi et al., "Cell toxicity of superparamagnetic iron oxide nanoparticles," Journal of Colloid and Interface Science, Aug. 15, 2009, 336(2):510-8.
Mahmoudi et al., "Emerging understanding of the protein corona at the nano-bio interfaces," Nano Today, Dec. 1, 2016, 11(6):817-32.
Mahmoudi et al., "Identification of nanoparticles with a colorimetric sensor array," ACS Sensors, Jan. 22, 2016, 1(1):17-21.
Mahmoudi et al., "Irreversible changes in protein conformation due to interaction with superparamagnetic iron oxide nanoparticles," Nanoscale, 2011, 3(3):1127-38.
Mahmoudi et al., "Optimal design and characterization of superparamagnetic iron oxide nanoparticles coated with polyvinyl alcohol for targeted delivery and imaging," The Journal of Physical Chemistry B, Nov. 20, 2008, 112(46):14470-81.
Mahmoudi et al., "Superparamagnetic iron oxide nanoparticles (SPIONs): development, surface modification and applications in chemotherapy," Advanced Drug Delivery Reviews, Jan. 2011, 63(1-2):24-46.
Mahmoudi et al., "Superparamagnetic iron oxide nanoparticles with rigid cross-linked polyethylene glycol fumarate coating for application in imaging and drug delivery," The Journal of Physical Chemistry C, May 14, 2009, 113(19):8124-31.
Mahmoudi et al., "Temperature: the "ignored" factor at the nanobio interface," ACS Nano, Aug. 27, 2013, 7(8):6555-62.
Mahmoudi et al., "Variation of protein corona composition of gold nanoparticles following plasmonic heating," Nano Letters, Jan. 8, 2014, 14(1):6-12.
McCloskey et al., "Magnetic cell separation: characterization of magnetophoretic mobility," Analytical Chemistry, Dec. 15, 2003, 75(24):6868-74.
Mirica et al., "Measuring densities of solids and liquids using magnetic levitation: fundamentals, Journal of the American Chemical Society," Jul. 29, 2009, 131(29):10049-58.
Mirica et al., "Using magnetic levitation for three dimensional self-assembly," Advanced Materials, Sep. 22, 2011, 23(36):4134, 4 pages.
Mirshafiee et al., "Impact of protein pre-coating on the protein corona composition and nanoparticle cellular uptake," Biomaterials, Jan. 1, 2016, 75:295-304.
Monopoli et al. "Biomolecular coronas provide the biological identity of nanosized materials," Nature Nanotechnology, Dec. 2012, 7(12):779, 27 pages.
PCT International Preliminary Report on Patentability in International Appln. No. PCT/US2019/042929, dated Jan. 26, 2021, 10 pages.

PCT International Search Report and Written Opinion in International Appln. No. PCT/US2019/042929, dated Oct. 4, 2019, 15 pages.
Pepe et al., "Phases of biomarker development for early detection of cancer," Journal of the National Cancer Institute, Jul. 18, 2001, 93(14):1054-61.
Petricoin et al., "SELDI-TOF-based serum proteomic pattern diagnostics for early detection of cancer," Current Opinion in Biotechnology, Feb. 1, 2004, 15(1):24, 4 pages.
Quillin et al., "Accurate calculation of the density of proteins," Acta Crystallographica Section D: Biological Crystallography, Jul. 1, 2000, 56(7):791-4.
Rahman et al., "Disease specific protein corona," Colloidal Nanoparticles for Biomedical Applications X, International Society for Optics and Photonics, Mar. 12, 2015, 9338, 93380V1-8.
Rubio-Perez et al., "In silico prescription of anticancer drugs to cohorts of 28 tumor types reveals targeting opportunities," Cancer Cell, Mar. 9, 2015, 27(3):382-96
Saha et al., "Regulation of macrophage recognition through the interplay of nanoparticle surface functionality and protein corona," ACS Nano, Apr. 26, 2016, 10(4):4421-30.
Sakulkhu et al., "Protein corona composition of superparamagnetic iron oxrde nanoparticles with various physico-chemical properties and coatings," Scientific Reports, May 21, 2014, 4(1):1-9.
Salvador-Morales et al., "Immunocompatibility properties of lipid-polymer hybrid nanoparticles with heterogeneous surface functional groups," Biomaterials, Jan. 2009, 30(12): 2231-2240.
Sansapour et al., "Nanoparticles affect bacterial colonies' optical diffraction patterns," Nanoscale, Jan. 2019, 11(6):2594-601.
Serpooshan et al., "Effect of cell sex on uptake of nanoparticles: the overlooked factor at the nanobio interface," ACS Nano, Mar. 14, 2018, 12(3):2253-66.
Shapiro et al., "Magnetic levitation as a platform for competitive protein-ligand binding assays," Analytical Chemistry, Jul. 17, 2012, 84(14):6166-72.
Sharifi et al., "Superparamagnetic iron oxide nanoparticles for in vivo molecular and cellular imaging," Contrast Media & Molecular Imaging, Sep. 2015, 10(5):329-55.
Shi et al., "Cancer nanomedicine: progress, challenge and opportunities," Nature Reviews Cancer, Jan. 2017, 17(1):20-37.
Smith et al., "American Cancer Society guidelines for the early detection of cancer," CA: A Cancer Journal for Clinicians, Jan. 2002, 52(1):8-22.
Suslick et al., "Discrimination of complex mixtures by a colorimetric sensor array: coffee aromas," Analytical Chemistry, Mar. 1, 2010, 82(5):2067-73.
Tan et al., "Serum autoantibodies as biomarkers for early cancer detection," The FEBS Journal, Dec. 2009, 276(23):6880-904.
Thomas et al., "High gradient magnetic separation of cells on the basis of expression levels of cell surface antigens," Journal of Immunological Methods, Oct. 2, 1992, 154(2):245-52.
Turker et al., "Recent advances in magnetic levitation: A biological approach from diagnostics to tissue engineering," ACS Biomaterials Science & Engineering, Feb. 6, 2018, 4(3):787-99.
Uniprot Consortium, "UniProt: a hub for protein information," Nucleic Acids Research, Oct. 27, 2014, 43:D204-12.
Weber et al., "Specific blood purification by means of antibody-conjugated magnetic microspheres," Scientific and Clinical Applications of Magnetic Carriers, Jan. 1997, 371-78.
Welter et al., "The NHGRI GWAS Catalog, a curated resource of SNP-trait associations," Nucleic Acids Research, Jan. 1, 2014, 42(D1):D1001-6.
Whitesides et al., "Magnetic separations in biotechnology," Trends in Biotechnology. Nov. 1, 1983, 1(5):144-8.
Wright et al., "Genetic diagnosis of developmental disorders in the DDD study: a scalable analysis of genome-wide research data," The Lancet, Apr. 4, 2015, 385(9975):1305-14.
Wulfkuhle et al., "Proteomic applications for the early detection of cancer." Nature Reviews Cancer, Apr. 2003, 3(4):267-75.
Zhang et al., "Identification of pathogenic fungi with an optoelectronic nose," Analyst, Apr. 16, 2014, 139(8):1922-8.

(56) References Cited

OTHER PUBLICATIONS

Zhao et al., "Label-free and continuous-flow ferrohydrodynamic separation of HeLa cells and blood cells in biocompatible ferrofluids," Advanced Functional Materials, Jun. 2016, 26(22):3990-8.

Zhao et al., "Label-free microfluidic manipulation of particles and cells in magnetic liquids," Advanced Functional Materials, Jun. 2016, 26(22):3916-32.

Zheng et al., "Multiplexed electrical detection of cancer markers with nanowire sensor arrays," Nature Biotechnology, Oct. 2005, 23(10):1294-301.

\* cited by examiner

200A

→ Gadovist Media 202

→ Plasma Proteins 204

→ Glass Tube 110

200B

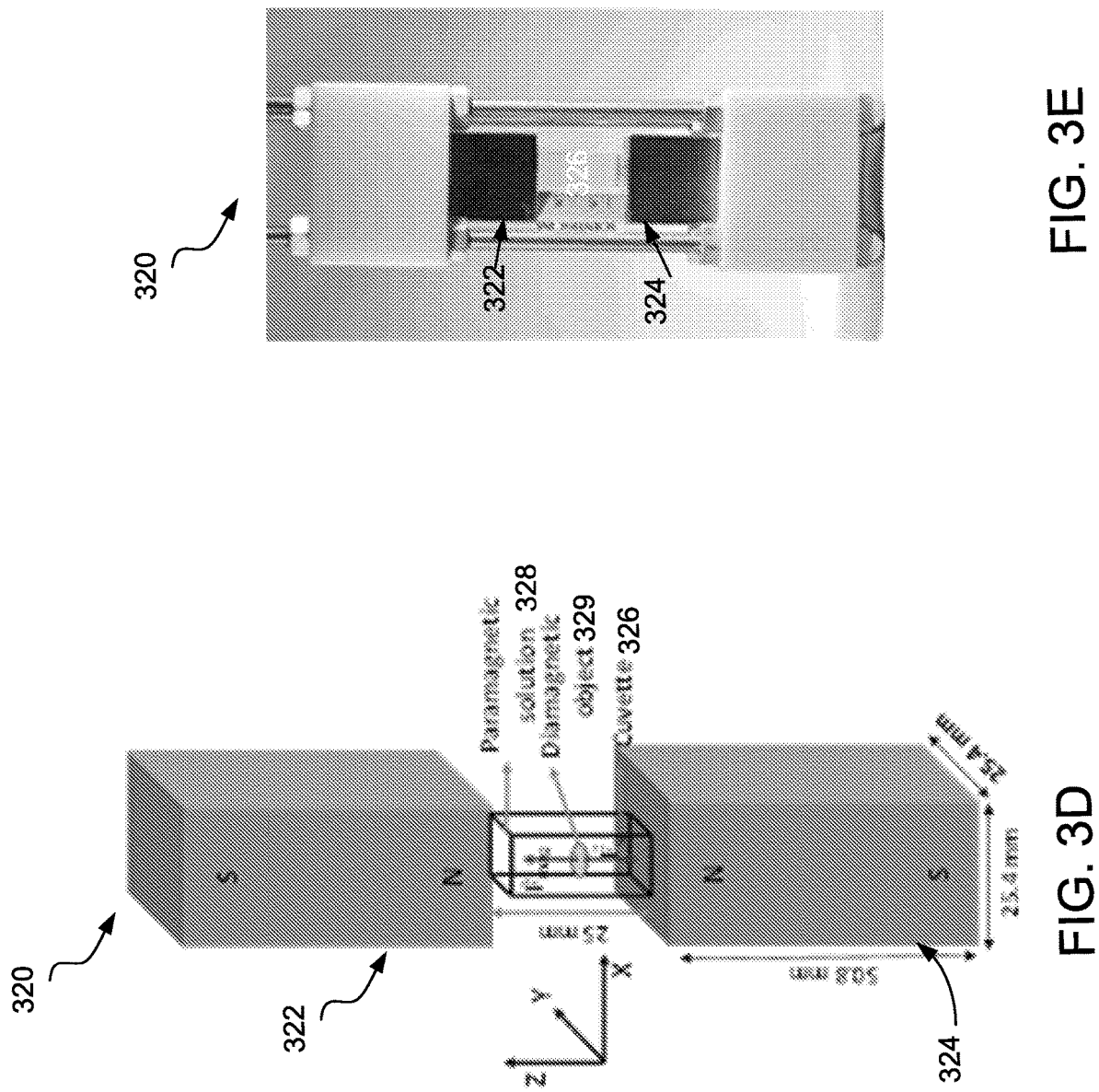

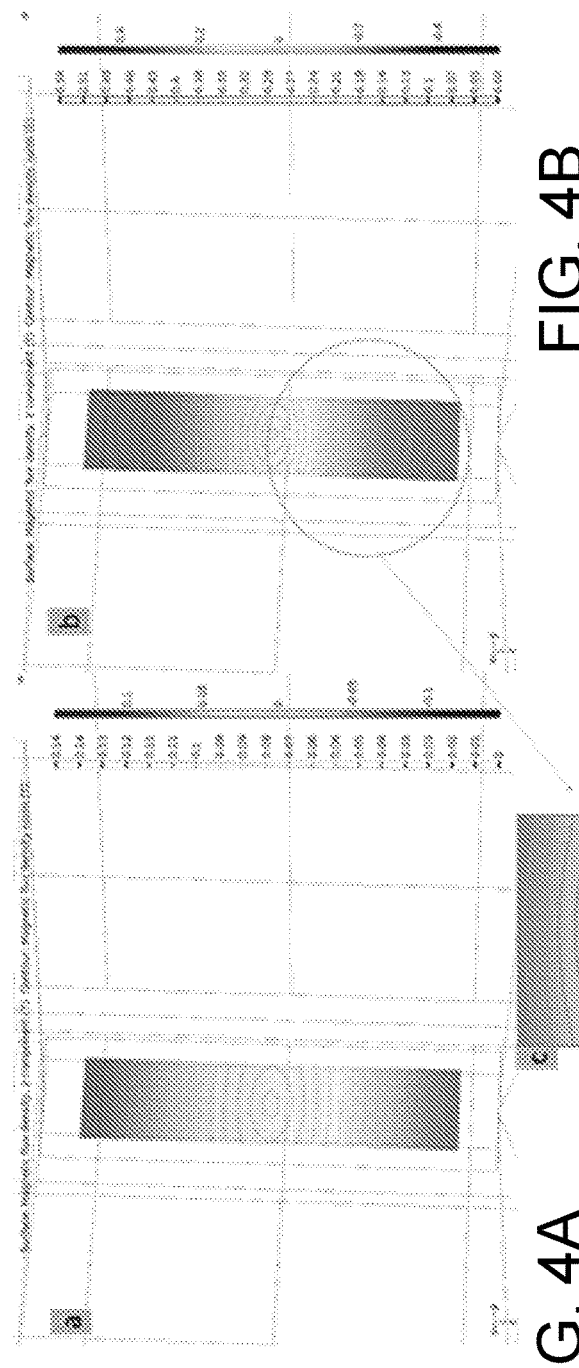
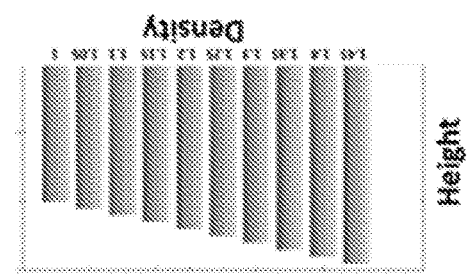
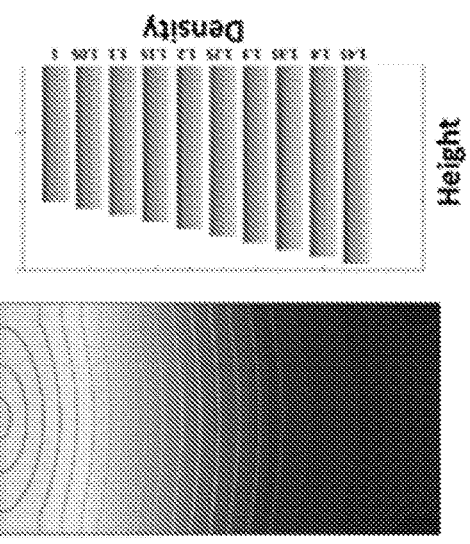
FIG. 4A
FIG. 4B
FIG. 4C

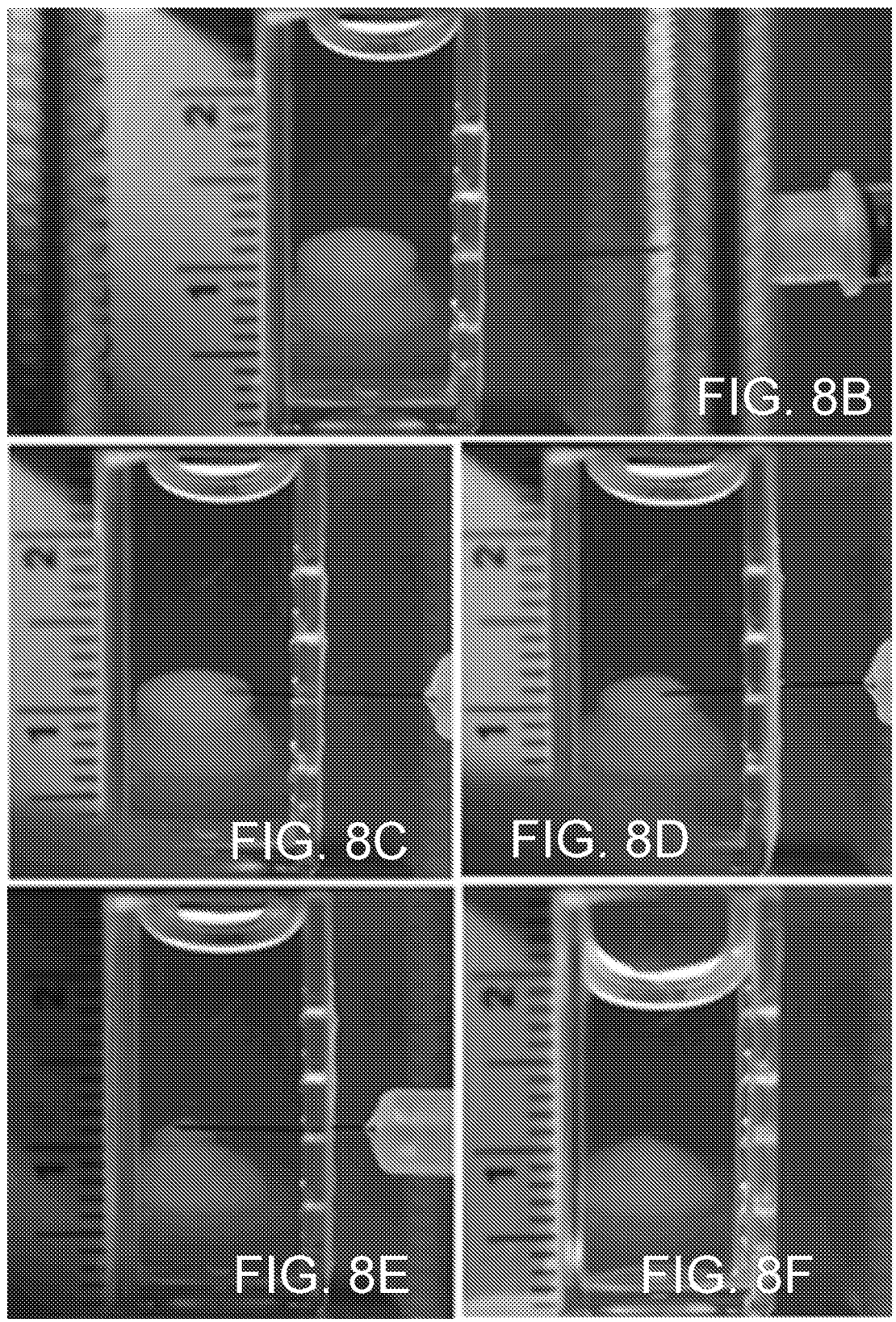

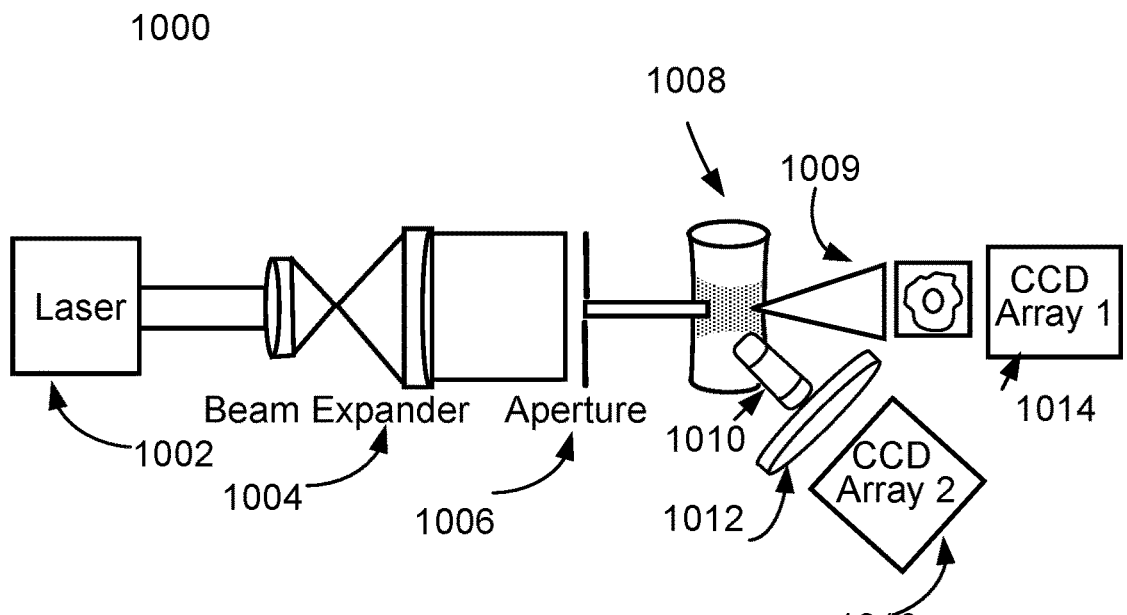
FIG. 10A
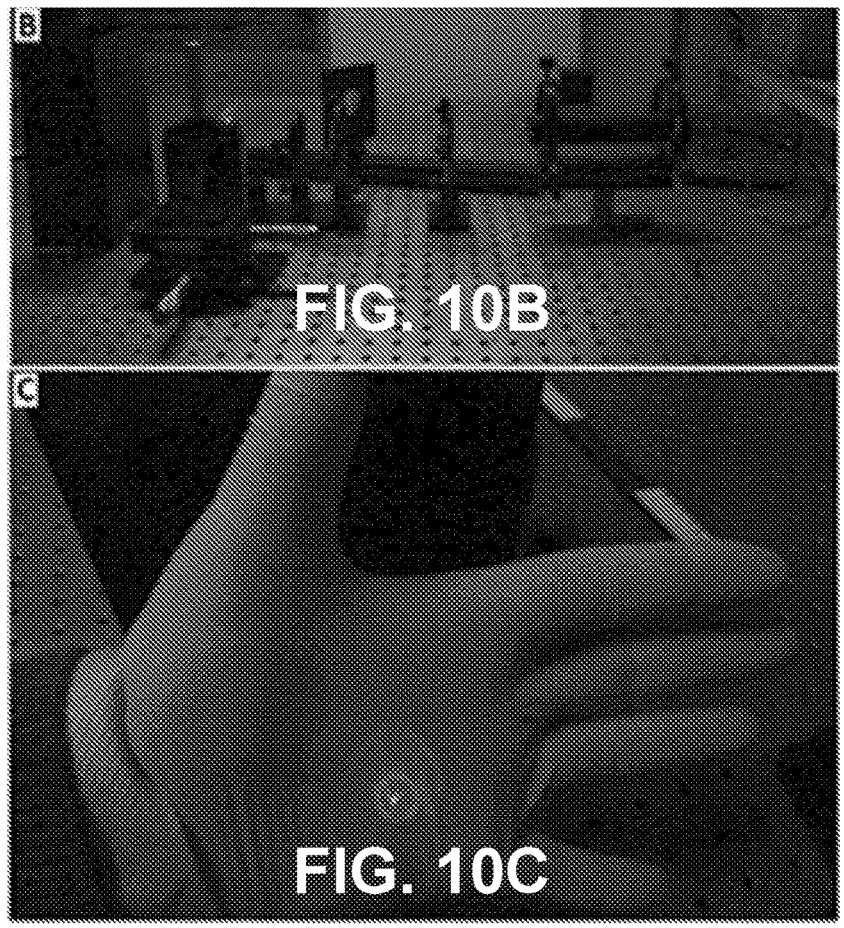

MAGNETIC LEVITATION TECHNIQUES TO SEPARATE AND ANALYZE MOLECULAR ENTITIES

CLAIM OF PRIORITY

This application is a National Stage application under 35 U.S.C. § 371 of International Application No. PCT/US2019/042929, having an International Filing Date of Jul. 23, 2019, which claims the benefit of U.S. Provisional Application Ser. No. 62/701,925, filed on Jul. 23, 2018 and U.S. Provisional Application Ser. No. 62/807,473, filed on Feb. 19, 2019. The entire contents of the foregoing are incorporated herein by reference.

TECHNICAL FIELD

This disclosure describes proteomic technologies for separating and analyzing biomolecules such as plasma proteins.

BACKGROUND

The composition of circulating plasma biomolecules (e.g., proteins) is dynamic over a spectrum of healthy and pathological conditions. Advances in the fields of proteomics are still awaiting translation into a suitable platform for early detection of, for example, Alzheimer's disease (AD).

SUMMARY

In one aspect, some implementations provide system for separating a plurality of molecular entities with differing densities. The system including: a pair of magnetic poles of like polarity to provide a magnetic field; and a container holding the plurality of molecular entities in a fluid medium comprising nanoparticles that substantially change a magnetic susceptibility of the fluid medium while preserving a stability of the molecular entities such that, when the container is placed inside the magnetic field, sufficient gradients in an effective density of the fluid medium are generated inside the container to levitate the plurality of molecular entities to respective layers within the container, each respective layer corresponding to a respective density.

Implementations may include one or more of the following features.

The nanoparticles may include at least one of: superparamagnetic iron oxide nanoparticles (SPIO), monocrystalline iron oxide nanoparticles (MIONs), Ultrasmall Superparamagnetic Iron Oxides (USPIOs), or a type of ferromagnetic or ferrimagnetic nanoparticles. The type of ferromagnetic or ferrimagnetic nanoparticles may include at least one of: a yttrium iron garnet, a cubic ferrite; and a hexagonal ferrite. The fluid medium may include at least one of: a superparamagnetic nanoparticle ferrofluid, a ferromagnetic nanoparticle ferrofluid, or a ferrimagnetic nanoparticle ferrofluid.

The nanoparticles may not be attached or bound to at least portions of the plurality of molecular entities. The nanoparticles may be attached or bound to at least portions of the plurality of molecular entities. A concentration of the nanoparticles in the fluid medium is about 0.001 mg/ml to about 30 mg/ml The pair of magnetic poles may be separated by a distance accommodating the container. The distance may be about 0.005 cm to 50 cm. The magnetic field is about 0.002 Tesla to 10 Tesla.

The container comprises a port to allow extraction of at least portions of a respective layer of the plurality of molecular entities from the container.

The system may further include an imaging system comprising one or more camera devices configured to perform image-based detection of the plurality of molecular entities levitated to the respective layers within the container.

The system may further comprise a laser system that includes: a laser source configured to generate a laser beam; passive optical components configured to guide the laser beam to irradiate the container; and one or more detectors configured to record an optical signal from the respective layers in response to being irradiated by the laser beam. The laser source may include a laser diode. The laser diode may output an optical power between 1 mW and 30 mW with an optical wavelength between 400 nm and 1300 nm. The passive optical components may include at least one of: a beam expander, an aperture, a grating, or a fiber. The one or more detectors may include at least one charge-coupled device (CCD).

In another aspect, some implementations provide a method for separating a plurality of molecular entities with differing densities. The method includes: introducing the plurality of molecular entities into a fluid medium comprising nanoparticles; and subsequently placing the fluid medium in a magnetic field to generate sufficient gradients in an effective density of the fluid medium such that the plurality of molecular entities are levitated to respective layers by virtue of the respective densities.

Implementations may include one or more of the following features.

The method may further include: extracting at least a portion of a respective layer comprising at least one of the plurality of molecular entities; and analyzing the portion of the respective layer using a technique for proteomics, lipidomics, or metabolomics. The technique for proteomics, lipidodmics, or metabolomics may include at least one of: a liquid chromatography mass spectroscopy (LC-MS/MS) technique, or a gel-electrophoresis technique.

The method may further include adjusting a concentration of the nanoparticles in the fluid medium to change a separation of the respective layers, wherein the concentration vary from about 0.001 mg/ml to about 30 mg/ml. The nanoparticles may include at least one of: superparamagnetic iron oxide nanoparticles (SPIO), Ultrasmall Superparamagnetic Iron Oxides (USPIOs), or a type of ferromagnetic or ferrimagnetic nanoparticles. The type of ferromagnetic or ferrimagnetic nanoparticles may include at least one of: a yttrium iron garnet, a cubic ferrite, and a hexagonal ferrite. The fluid medium may include at least one of: a superparamagnetic nanoparticle ferrofluid, a ferromagnetic nanoparticle ferrofluid, or a ferrimagnetic nanoparticle ferrofluid. The nanoparticles may not be attached to at least portions of the plurality of molecular entities. The nanoparticles may not be attached or bound to at least portions of the plurality of molecular entities.

The method may further include optically resolving the respective layers of the plurality of molecular entities to perform image-based detection of the plurality of molecular entities levitated to the respective layers within the container. Placing the fluid medium in the magnetic field may occur at a first time point. Optically resolving the respective layers of molecular entities may occur at a second time point. The first time point may precede the second time point by about 10 seconds to 10 hours.

Optically resolving may include: energizing a laser source to generate a laser beam; irradiating each of the respective layers with the laser beam; and recording an optical signal from each of the respective layers in response to being irradiated by the laser beam. The laser beam may be characterized as having an optical power between 1 mW and 30 mW and an optical wavelength between 400 nm and 1300 nm. The magnetic field may be characterized as having a field strength of about 0.002 Tesla to 10 Tesla.

Other features and advantages of the invention will be apparent from the following detailed description and figures, and from the claims.

DESCRIPTION OF DRAWINGS

FIG. 3A to 3G shows various examples of a MagLev platform.

FIG. 4A-C show examples of magnetic field distributions in a medium and a corresponding distribution of plasma proteins in the height direction of a MaLev platform.

FIGS. 8A-H show examples of analyzing a particular band of plasma protein using the MagLev system with improved resolutions.

FIGS. 10A-C show examples of an optical system to measure the distinct layers of plasma proteins using laser diffraction patterns.

DETAILED DESCRIPTION

Figure 1:
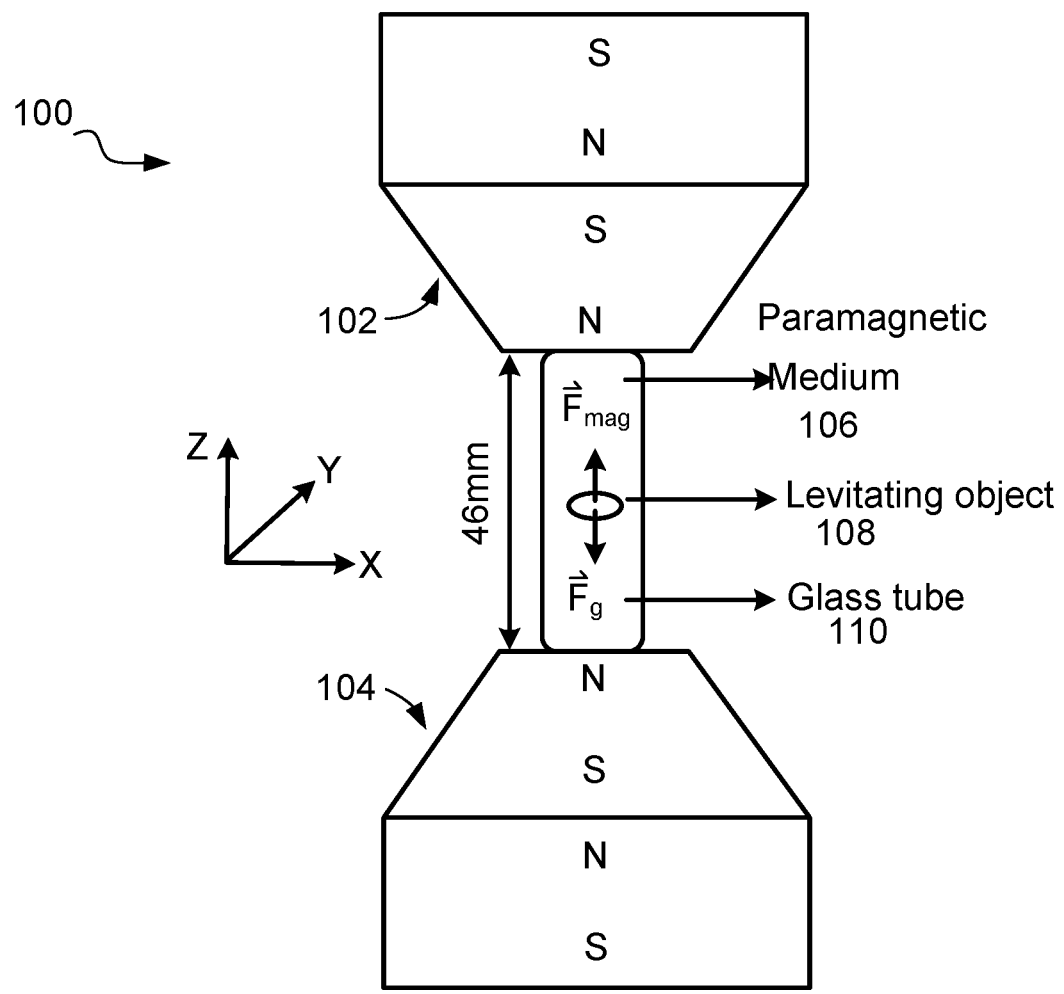
FIG. 1 is an example of a schematic diagram for a magnetic levitation (MagLev) system.

The present disclosure describes systems and methods that use magnetic levitation (MagLev) to separate human plasma proteome, thereby detecting dissimilarities between the plasma composition of healthy control subjects and disease (e.g., AD) groups. The ability to differentiate control subjects and disease groups can be leveraged for diagnosis (e.g., determining likelihood of AD) and prognosis purposes (e.g., predicting progression of AD). While some MagLev systems accomplish separations by competing gravitational and magnetic forces experienced by diamagnetic particles suspended in a paramagnetic liquid medium, the present disclosure reveals the use of, for example, superparamagnetic iron oxide nanoparticles, to substantially enhance the susceptibility of a magnetic medium, for example, phosphate-buffered saline (PBS) with varying concentrations of superparamagnetic iron oxide nanoparticles (SPIONs), and subsequently enable the MagLev systems to generate strong and continuous gradients in effective density to separate plasma macromolecules (such as proteins, lipids, metabolomes) and other biological fluids (e.g., urine, tear, and interstitial fluid) due to their subtle density variations. The system may also operate on protein-protein interactions causing differences in overall protein 3D conformations. The system may also levitate some types of nanoparticles (such as aluminum oxide ($Al_2O_3$), indium oxide, tungsten oxide, silver, and gold) for quality control purposes. Such biomolecules and nanoparticles may be jointly referred to as molecular entities. As discussed in more detail below, examples of a MagLev system have unique capacities to separate plasma proteins in liquid phase. For example, using superparamagnetic liquid in which distinct magnetic flux density is created, various types of plasma proteins (e.g., sub-micron biological entities or macromolecules) can be separated into relevant range of densities according to acceptable kinetics of separation. The resolution of the plasma proteins levitated into different bands can be advantageously increased by altering the magnetic field and the composition of superparamagnetic liquid. In addition, substantial differences are demonstrated between MagLev created plasma protein profiles (both by mass spectroscopy and optical images) of healthy individuals and AD patients.

Indeed, the disclosed systems and methods allow proteomics approaches to robustly define or identify important proteins which may reflect the progress (or stages) of a disease, such as AD, where macromolecules are altered due to disease onset and subsequent progression. Defining these protein entities is advantageous not only for developing new diagnostic devices but also for drug discovery to prevent or slow down the progression of, for example, AD. In particular, separation of plasma proteins tackles challenges resulting from the vast dynamic range and high complexity of the plasma proteome and therefore can overcome the major challenge in the field of proteomics. Moreover, the identified promising proteins may be further examined to evaluate, for example, whether the expression of their respective genes in the brain correlates with AD pathology (e.g., degree or stages) as potential biomarkers. For example, the separated proteins can be further analyzed with liquid chromatography mass spectroscopy. Such evaluations may be conducted by quantifying expression of selected genes using quantitative polymerase chain reaction (qPCR) and comparative transcriptomics. Finally, both optical images and diffraction pictures can be inspected to improve diagnosis and prognosis because the achieved plasma bands in the MagLev system may provide a "fingerprint" pattern for differentiating, for example, healthy individuals and AD patients. In addition to identifying a subpopulation more prone to a particular disease, these capabilities can identify novel protein markers, and their respective genes, for example, in the brain that are related to early stage development of AD. Such identification can incorporate a full complement of algorithms including, for example, machine learning approaches.

FIG. 1 shows an example of a schematic of a magnetic levitation (MagLev) system 100. The MagLev system 100 includes a pair of magnets, namely, magnet 102 and magnet 104 facing each other with a pole of the same kind. In this example, magnets 102 and 104 have north poles facing each other along the vector of gravity. Additionally or alternatively, magnets 102 and 104 can have south poles facing each other along the vector of gravity. The magnetic field between the poles of magnets 102 and 104 can be from about 0.002 Tesla to 10 Tesla. As illustrated, a magnetic field is generated within a distance of 46 mm between the two poles facing each other. The distance can be from about 0.005 cm to 50 cm. This magnetic field can operate on a magnetic object to counteract the effects of gravitational acceleration, as will be further explained below. A glass tube 110 is placed within the distance. In one example, paramagnetic medium 106 fills the glass tube 110. In general, a paramagnetic medium is an aqueous solution of a paramagnetic liquid such as MnCl2, GdCl2, Gadovist, ZnCl2, etc. with different concentrations ranging from 0.1M to 2M. In other examples, a magnetic medium comprising phosphate-buffered salines (PBS) and superparamagnetic iron oxide nanoparticles (SPIONs) may fill the glass tube 110, as will be further discussed below, for example, in association with FIG. 2. The MagLev system 100 is unrelated to implementations of immunoadsorption using superparamagnetic, ferromagnetic, or ferrimagnetic particles. In MagLev system 100, the magnetic field between the two poles facing each other repels diamagnetic plasmas proteins away from areas of high magnetic field and cancel out their gravitational forces, causing levitating object 108 to be in a suspension mode. These plasma proteins are subject to competing magnetic force ($F_{mag}$) and gravitational force ($F_g$), and without requiring labeling. In contrast to the MagLev system 100, in implementations of immunoadsorption, ferromagnetic or superparamagnetic particles are attached to desired cells and the labeled cells will be attracted to the area of high field.

Diamagnetic materials levitate in the MagLev system when the gravitational force acting on the diamagnetic sample is balanced by the magnetic force produced through the paramagnetic medium because of an external applied magnetic field. The physics and theory describing this balance can be summarized by equation 1 below.

$$h = \frac{(\bar{\rho}_s - \rho_m)g\mu_o d^2}{(\bar{\chi}_s - \chi_m)4B_0^2} + \frac{d}{2} \quad (1)$$

Equation 1 relates the density of the levitating sample to its equilibrium levitation height h (m). In this equation, $\rho_m$ and $\rho_s$ (kg/m$^3$) are the density of the paramagnetic medium and sample respectively, g is the gravitational acceleration, $\mu_0$ (T.m.A$^{-1}$) is the permeability of free space, d (m) is the distance between the magnets, $B_0$ (tesla) is the magnitude of the magnetic field at the surface of the magnets, $\chi_m$ and $\chi_s$ are the magnetic susceptibilities of the paramagnetic medium and the sample, respectively.

The separation capacity of the MagLev system 100 derives from the magnetic force principle. This separation capacity can separate non-biological and biological species depending on their density differences within a three-dimensional space. For context, the density of proteins is strongly dependent on the protein structures, conformation, and layer of immobilized water on their surfaces. Therefore, technologies capable of separating proteins according to their density variation can overcome some of the challenges in the field of proteomics and provide an excellent opportunity to detect important biomarkers that correlate well with the occurrence and progress of a disease, such as Alzheimer's disease (AD). In this context, the separation and optional identification of biomolecules (such as proteins and metabolites, for example, in plasma) remains challenging; the present specification discloses a combination of superparamagnetic iron oxide nanoparticles and magnetic fields to separate biomolecules by density. Additionally or alternatively, a ferrofluid can be introduced with a unique capacity to localize the magnetic levitation in a nanometer scale and therefore minimize the random walk of the plasma proteins in liquid to provide an opportunity to separate proteins based on their density variations. For context, ferrofluids are colloidal liquids made of nanoscale ferromagnetic, or ferrimagnetic, particles suspended in a carrier fluid (usually an organic solvent or water). Each tiny particle can be thoroughly coated with a surfactant to inhibit clumping. Large ferromagnetic particles can be ripped out of the homogeneous colloidal mixture, forming a separate clump of magnetic dust when exposed to strong magnetic fields. The magnetic attraction of nanoparticles is weak enough that the surfactant's Van der Waals force is sufficient to prevent magnetic clumping or agglomeration. Ferrofluids usually do not retain magnetization in the absence of an externally applied field and thus are often classified as "superparamagnets" rather than ferromagnets. While FIG. 1 shows a pair of permanent magnets with like poles opposing each other, magnets of other configuration (e.g., different shapes or magnetic induction apparatus such as coils) can also be used. Such magnet can include, for example, superconducting magnet, and solenoid magnet.

The separated proteins may then be collected and be analyzed using a technique for proteomics, lipidomics, or metabolomics. An example of such a technique can be the liquid chromatography mass spectroscopy (LC-MS/MS) technique to identify the important proteins which may reflect the existence or progress of AD. Other examples can include a gel-electrophoresis technique. In some cases, sodium dodecyl sulfate-polyacrylamide gel electrophoresis (SDS-PAGE) analysis can be performed on the separated proteins. In addition, a laser diffraction system can be used to inspect the achieved plasma bands in the MagLev system 100 as such bands may provide a "fingerprint" patterns for the healthy individuals and diseased patients (such as AD patients).

Figure 2A:
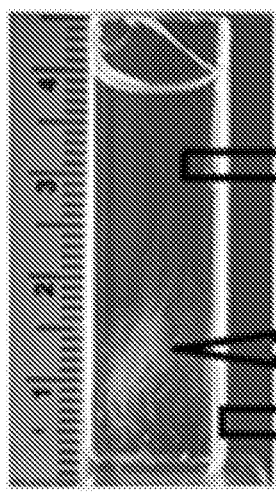
FIGS. 2A-B are examples of images showing human plasma in the MagLev system of FIG. 1 with Gadovist paramagnetic media at, respectively, 1 min and 1 hour after plasma injection.
Figure 2B:
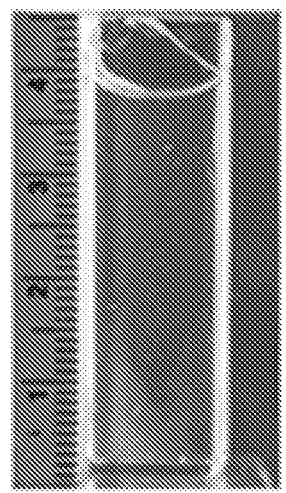

FIGS. 2A-B are examples of images respectively showing human plasma exposed to the MagLev system 100 with Gadovist paramagnetic media 202 at 1 min (200A) and 1 hour (200B) after injection of human plasma. Although paramagnetic media could be used to separate different cell types, such media may not be used for smaller biological entities like proteins and other types of plasma biomolecules including lipids and metabolomes. As shown in FIGS. 2A-B, even the Gadovist media (which can be a promising biocompatible paramagnetic media), when used in the MagLev system 100 (and in glass tube 110), may not have a capacity to separate plasma macromolecules such as proteins, lipids and metabolomes (mainly due to the relatively huge effects of Brownian motions on biomolecules such as proteins and metabolomes). Instead, the plasma macromolecules were settled down in the glass tube 110. No levitation has been demonstrated for these plasma macromolecules. Between 1 minute of settling (200A) and 1 hour of settling (200B), plasma macromolecules 204 remained an undifferentiated mass towards the bottom of glass tube 110.

EXAMPLES

The invention is further described in the following examples, which do not limit the scope of the invention described in the claims.

Example 1. MagLev Platforms

To address this issue and use the MagLev system 100 for macromolecule separation, superparamagnetic iron oxide nanoparticles (SPIONs), instead of the usual paramagnetic fluids, can be used to levitate biomolecules and proteins of human plasma. When placed inside a magnetic field, these SPIONs could induce a local magnetic field that affects biomolecules' Brownian motions and help these molecules to levitate to different positions in the liquid in response to the subtle density variation among these macromolecules. Additionally, monocrystalline iron oxide nanoparticles (MIONs), Ultrasmall Superparamagnetic Iron Oxides (US-PIOs), or a type of ferromagnetic or ferromagnetic nanoparticles can also be used. Examples of ferromagnetic or ferromagnetic nanoparticles include: a yttrium iron garnet, a cubic ferrite (e.g., aluminum, cobalt, nickel, manganese, and zinc), and a hexagonal ferrite ((e.g., $PbFe_{12}O_{19}$ and $BaFe_{12}O_{19}$)).

Figure 3A:
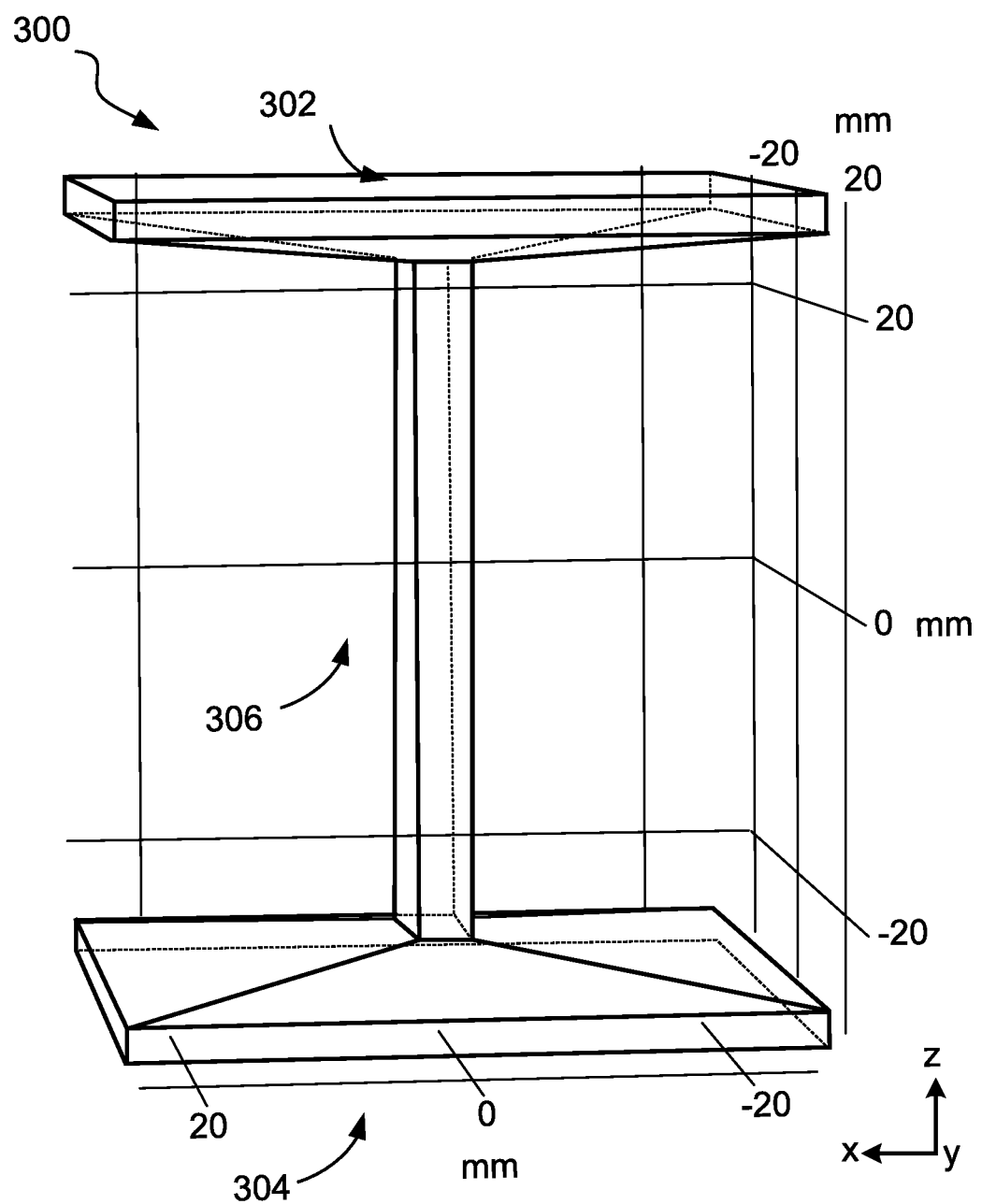

The levitation process can be modeled. The net applied forces on the objects in the solution with paramagnetic materials can be calculated. For context, the discussion is applicable to a solution with SPIOs and the levitating molecular entities are diamagnetic objects. Almost all of proteins are diamagnetic (except the ones that carry specific ions like iron—hemoglobin). FIG. 3A shows an example of a structure 300 for such modeling. This example of simulation demonstrates a sample holder placed between two magnets with poles of the same polarity. Considering the geometrical structure of experiment, the z-axis 306 shows the direction of gravity force (towards center of the Earth) and the magnetic force. Region 302 and region 304 represent the poles of the pair of magnets facing each other. As discussed earlier, the poles are of the same polarity. The following equations show the gravity force (considering the buoyancy effect) and the magnetic force applied on the particles respectively.

$$\vec{F}_g = (\rho - \rho_m)V\vec{g} \quad (2)$$

$$\vec{F}_m = \frac{(\chi - \chi_m)}{\mu_0}V(\vec{B}\cdot\vec{\nabla})\vec{B} \quad (3)$$

where $F_g$ and $F_m$ represent gravity and magnetic force respectively. $\rho$ and $\rho_m$ denote the density of the object and medium respectively. $\chi$ and $\chi_m$ are the magnetic susceptibility of the object and medium correspondingly. B shows the magnetic flux density and V represent the volume of the objects. $\mu_0$ is vacuum permeability and g is the gravitational constant. While the particles (such as plasma macromolecules) are levitated, the total force should be zero. By applying the zero condition to net force, the position of levitated particles can be determined according to the following equation:

$$h = \frac{(\rho - \rho_m)g\mu_0}{\alpha_z^2(\chi - \chi_m)} \quad (4)$$

where $\alpha_z$ represent the gradient of magnetic field in direction of z (direction of gravity force). For levitating objects, the effects (directly or indirectly) of the magnetic field in the z direction act to cancel out the weight of the object.

Figure 3C:
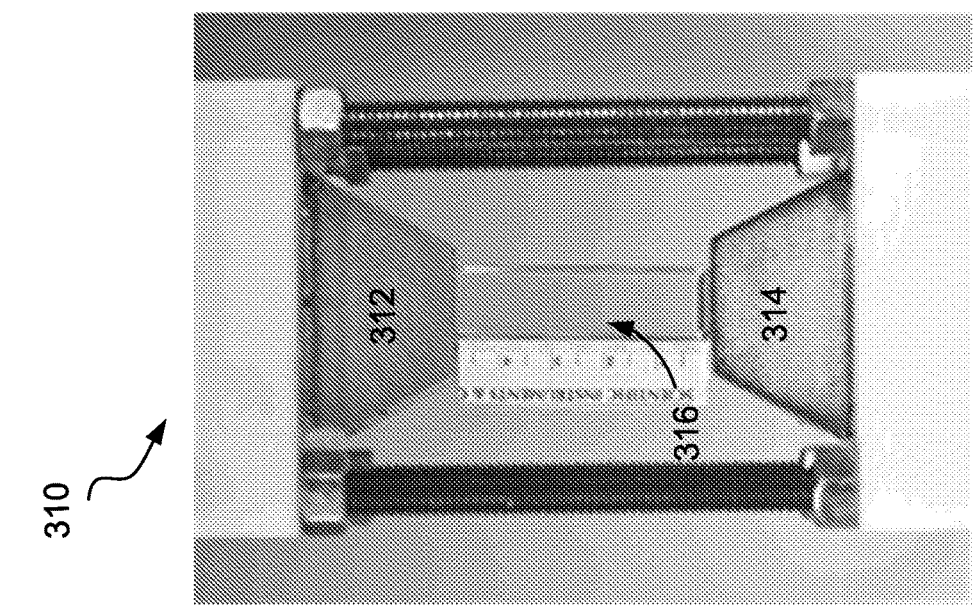
Figure 3B:
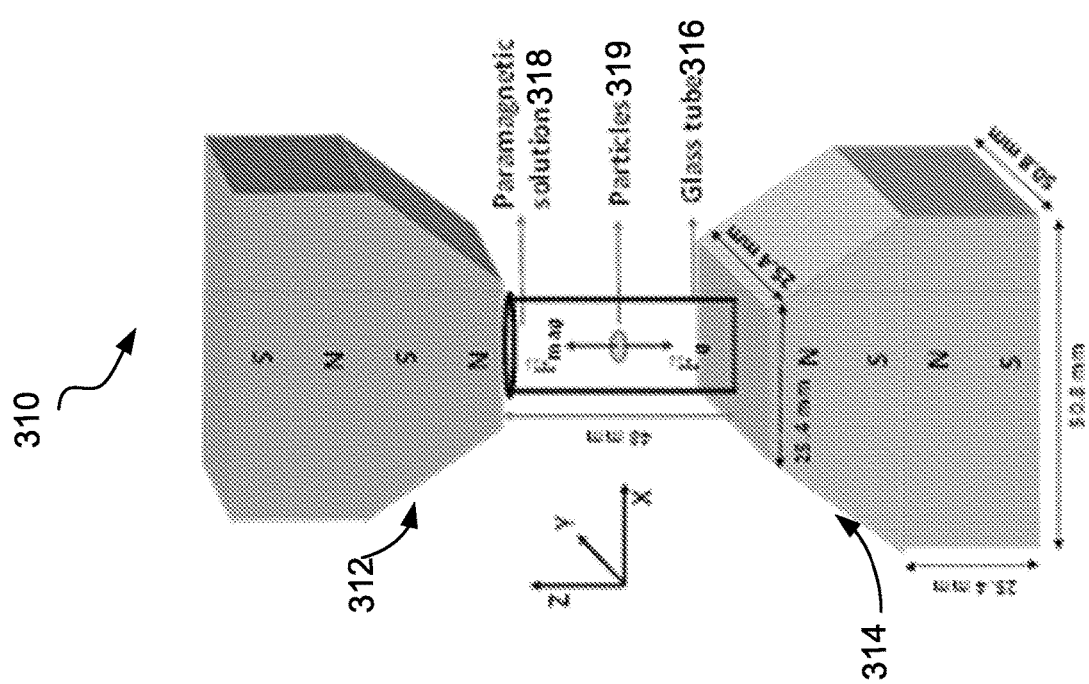
Figure 3G:
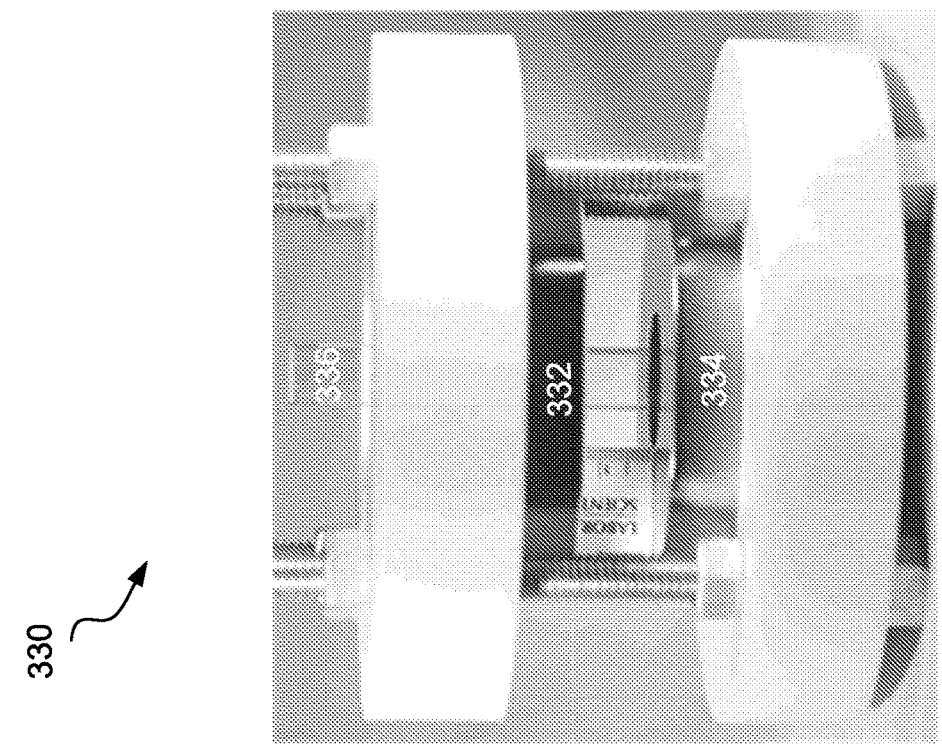
Figure 3F:
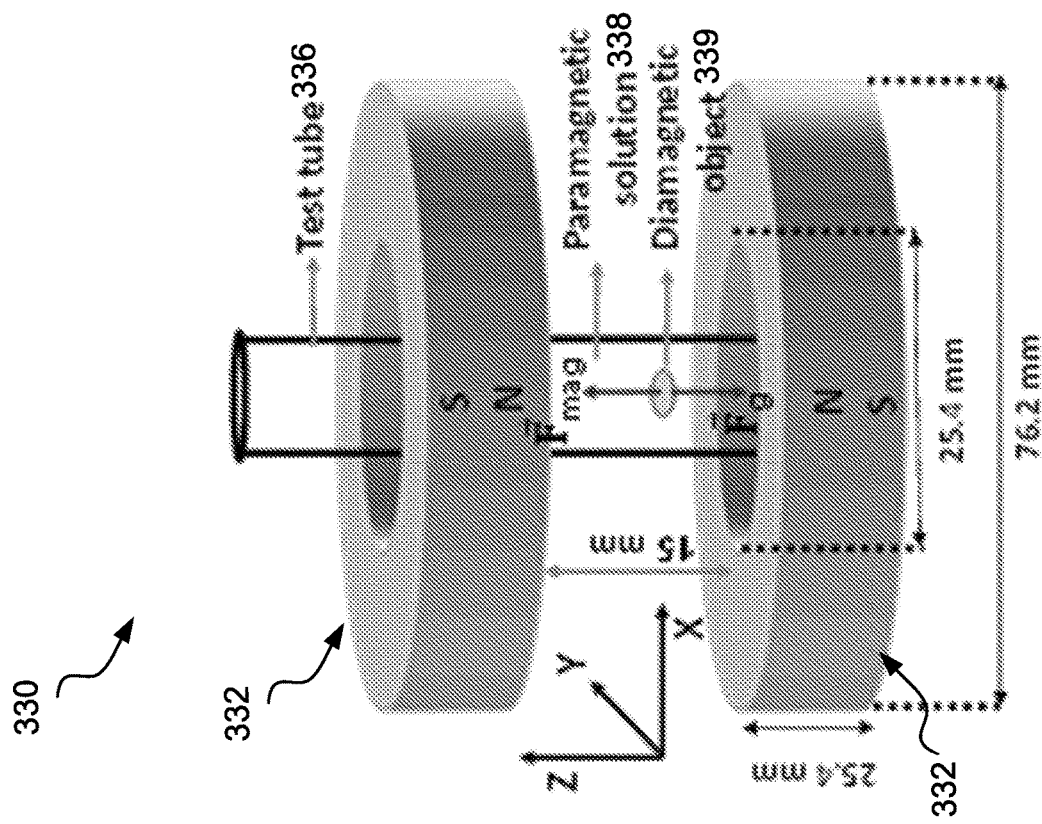

Referring to FIGS. 3B to G, examples of MagLev platforms are shown. FIGS. 3B and 3C are, respectively, schematic and photographic illustrations of a pyramid configuration 310 where the north poles of two magnets (312 and 314) are facing each other and separated by a distance of 48 mm, creating a magnetic field that covers a glass tube 316. The two magnets 312 and 314 include a pyramid portion with a trapezoid profile. Glass tube 316 contains a paramagnetic solution 318 in which particles 319 are being levitated through a balancing act between magnetic force $F_{mag}$ and gravitational force $F_g$. FIGS. 3D and 3E are, respectively, schematic and photographic examples of a standard configuration 320. The north poles of two magnets (322 and 324) are likewise facing each other and separated by a distance of 25 mm, creating a magnetic field that covers a cuvette 326. The two magnets 322 and 324 both have rectangular cross-sectional profiles. Cuvette 326 contains a paramagnetic solution 328 in which particles, such as diamagnetic objects 329, are being levitated through a balancing act between magnetic force $F_{mag}$ and gravitational force $F_g$. FIGS. 3F and 3G are, respectively, schematic and photographic examples of a ring configuration 330. The north poles of two magnets (332 and 334) are also similarly each other and separated by a distance of 15 mm, creating a magnetic field covering a test tube 336. The two magnets 332 and 334 both are ring annular configurations with donut profiles (e.g., inner diameter of 25.4 mm and outer diameter of 76.2 mm). Test tube 335 contains paramagnetic solution 338 in which particles, such as diamagnetic objects 339, are being levitated through a balancing act between magnetic force $F_{mag}$ and gravitational force $F_g$.

To obtain the related values based on the configuration shown in, for example, FIG. 3A, the distribution of values of magnetic flux density has been calculated using Finite Element Method (FEM) in COMSOL® Multiphysics software. The results are shown in FIG. 4, demonstrating examples of magnetic field distributions in a medium as well as a corresponding distribution of plasma proteins in the MagLev system 100 whose dimensions are outlined in FIG. 3A. Specifically, FIG. 4A shows the magnetic field gradients (along the direction of the gravity force) in a liquid medium of paramagnetic nanoparticles. In comparison, the SPIONs can change the magnetic field gradient in the liquid to further help levitation of biomolecules/proteins. FIG. 4B shows the magnetic field gradients with a much increased scale (e.g., approximately four folds) as seen in a liquid medium of SPIO nanoparticles (SPIONs). As discussed earlier in association with FIGS. 1, 2A-B, and equation (1), the levitation force generated in the paramagnetic medium is not sufficient to offset the effects of Brownian motions on biomolecules such as proteins and metabolomes. In contrast, the SPIONs provide much higher magnetic susceptibilities compared to the paramagnetic materials which facilitate the separation of biomolecules (such as plasma proteins) which have very small density differences in the glass tube of MagLev system 100 between the like poles of two permanent magnets. Based on the distribution of magnetic flux density between the two magnets in presence of the superparamagnetic fluid, FIG. 4C shows the relation between the height distribution of proteins and the corresponding densities of these proteins. Here, the inverse relation of height to the density of proteins is demonstrated (e.g., the higher density proteins will be levitated closer to a pole of the magnet and the lower density proteins will be levitated close to the center of the cuvette).

Example 2. MagLev for Macromolecules

Figure 5:
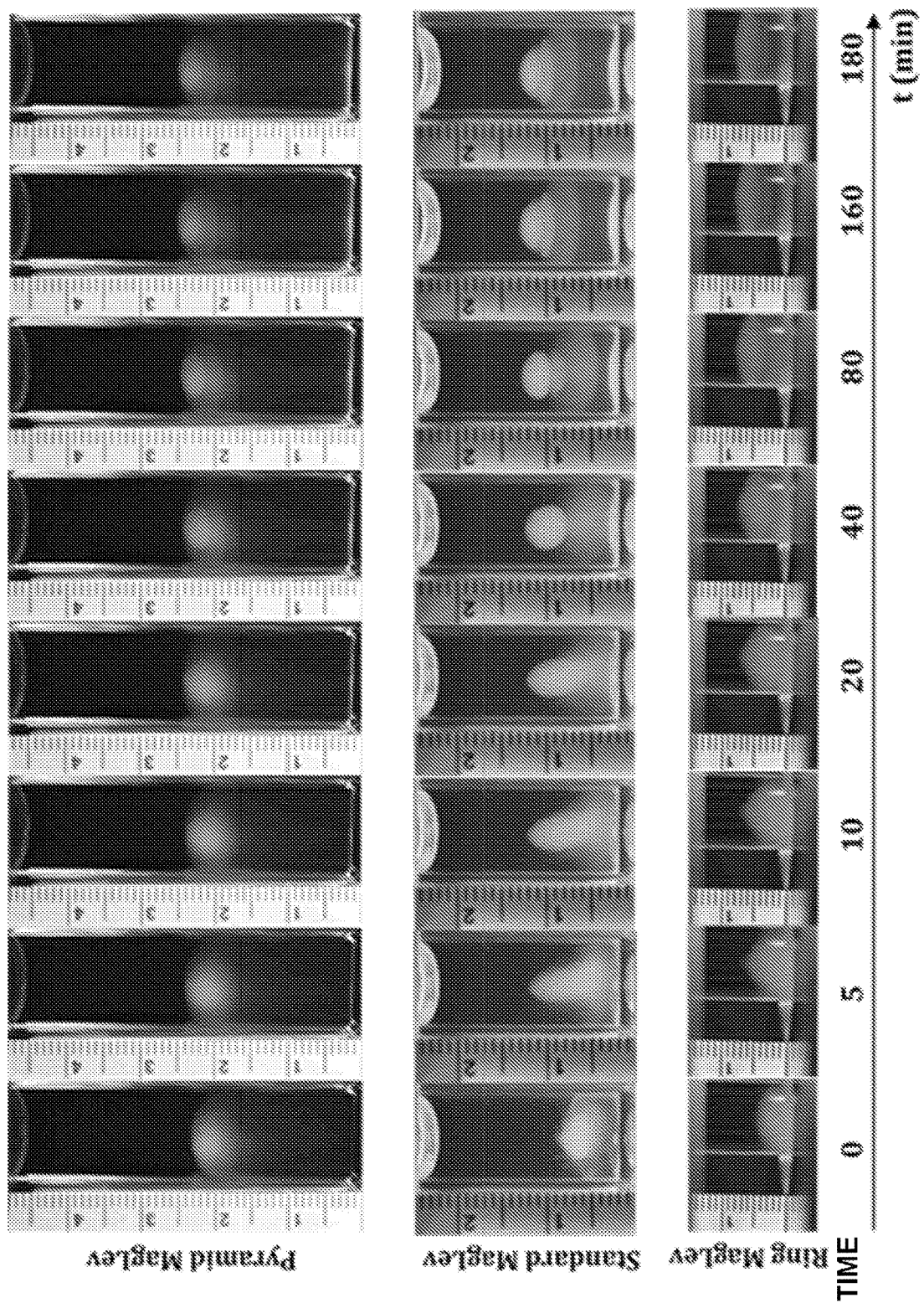
FIG. 5 shows examples of images depicting the formation of human plasma patterns profile in the MagLev system for up to 3 hours of settling.

The present methods can be used to purify low abundant and low molecular weight macromolecules (including proteins that are useful as biomarkers) efficiently, for example, in less than 10 minutes. Using SPIO nanoparticles, the disclosed techniques can separate and optionally identify plasma macromolecules in different categories; and the purified macromolecules in each category can be used for subsequent LC-MS/MS analysis which in turn can overcome a central issue of the proteomics approaches for detection of biomarkers. For example, a sample comprising 1-1000 µL, e.g., 10-100 µL, e.g., 20-50 µL, e.g., 40 µL, of human plasma from a healthy individual is mixed, e.g., injected into a medium with SPIONs. The concentration of SPIONs can range from about 0.001 mg/ml to about 30 mg/ml. Unlike with Gadovist media, a MagLev system using a medium comprising SPIONs can be used to generate a sharp and distinct protein patterns during an observation window that lasts 3 or more hours, as shown in the series of images of FIG. 5. These distinct patterns correspond to a variation of protein types. The stratified appearance takes shape during the initial period of this 3-hour window. After a period of 1 hour, the layers appear to reach a steady state without incurring significant changes. In particular, the top panel of FIG. 5 shows the formation of distinct patterns on the pyramid MagLev platform (with a 0.25 mg/ml concentration of SPIONs), while the middle panel and the bottom panel respectively show the formation of distinct patterns on the standard and ring platforms (both with 0.06 mg/ml concentration of SPIONs). Although the layers are progressively spreading with respect to time on all three platforms, the stratified appearance on the pyramid platform appears less developed than on the standard and ring platforms. Moreover, the lateral extent of the stratified appearance is more prominent on the ring platform than the standard platform. However, the stratified appearance of the top layers on the standard platform is more intense than on the ring platform. In various use cases, the settling time from the moment of getting exposed to the magnetic field to the moment of steady state separation can range from 10 seconds to 10 hours. This settling time can depend on a concentration of SPIONs in the medium, which can vary from about 0.001 mg/ml to about 30 mg/ml. The steady state separation can be reached when the stratified appearance becomes stable in shape (e.g., exhibiting less than 10% variation in overall area).

Example 3. MagLev for Diagnosis

Figure 6A:
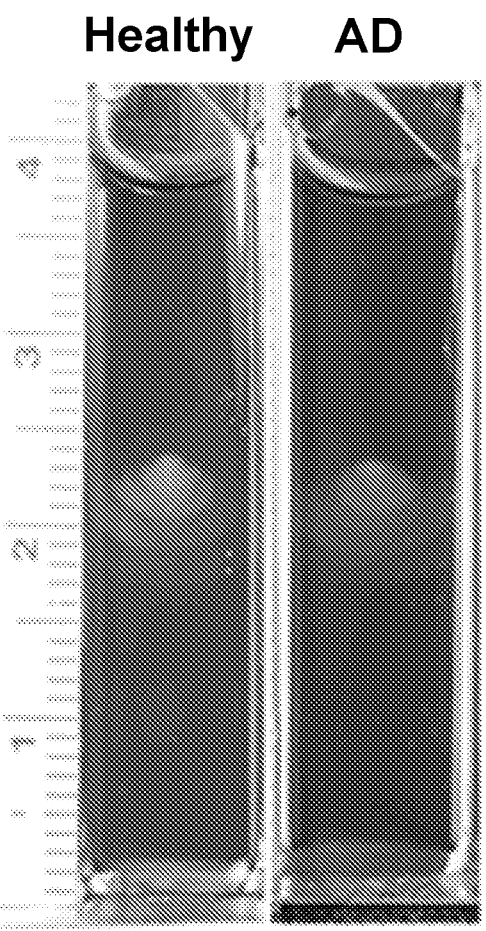
FIGS. 6A-B show examples of images depicting the formation of distinct human plasma patterns (from a healthy subject and an AD patient) in the MagLev system.
Figure 6B:
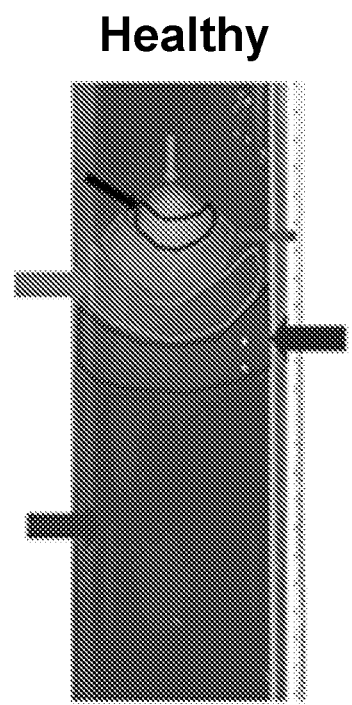

A wide range of disease biomarkers can be found in these protein bands in view of the absence of highly abundant proteins in some of the bands. As discussed earlier, proteins in a sample of human plasma will have different densities and therefore have different levitation heights in the MagLev system. By adding human plasmas, e.g., from healthy individuals, opioid addicted subjects, and subjects diagnosed with cancer to the MagLev system, a unique and distinct protein pattern was demonstrated for each group in a reproducible manner. FIGS. 6A-B show example of images depicting the formation of distinct patterns for human plasmas (from a healthy subject and an AD patient) in the MagLev system. In particular, the patterns from the healthy individual and the AD patient are different. While both images show similar sector appearances, the patterns from the healthy individual show larger and brighter bands than those from the AD patients. These unique patterns for each disease can thus improve early detection of disease even without the need for analyzing proteins/biomarkers. FIG. 6B is a zoomed-in view of the image of the healthy individual in FIG. 6A, further revealing fine structures within this control group.

Indeed, the formed protein layers can be collected, e.g., with microfluidic channels or one or more syringes, e.g., insulin syringes, that can enter the media through the side of the glass tube. The syringe needles can range from, for example, gauge 31 to gauge 18. The disclosed MagLev techniques can incorporate a variety of syringes from less than 1 cc to over 100 cc. The protein bands may then be individually analyzed by an LC-MS/MS technique. In some implementations, the outcomes have revealed detection of over 4000 proteins in healthy individuals and AD patients. Among those proteins, statistically significant differences have been observed in 137 proteins between plasmas from healthy individuals and AD patients. The associated genes may be defined which may have correlation with the identified proteins. To verify the role of the statistically significant proteins, the results were compared with Open Targets database (opentargets.org). As a platform for therapeutic target identification and validation, the Open Tables database calculates a disease-association score for each protein based on evidence from various other public databases (including GWAS Catalog, UniProt, Gene2Phenotype, Cancer Gene Census, IntOGen, Europe PMC, and Reactom) to derive a score on a scale of 0 (lowest) to 1.0 (highest) of disease association. Spectacularly, all of the identified significant proteins have association with AD. More specifically, 81 proteins have scores of 1; 31 proteins have scores between 0.7-1.0; and the remaining 25 proteins have scores between 0.3-0.7.

Example 4. MagLev with Improved Diagnosis and Proteomics

Figure 7A:
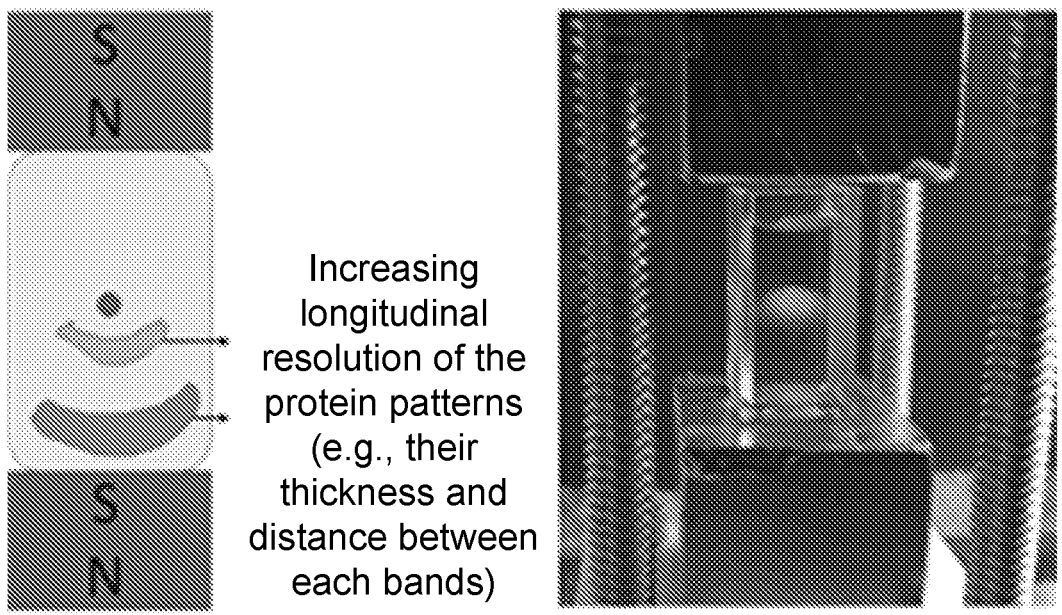
FIGS. 7A-E show examples of various aspects of the MagLev system to more advantageously resolve patterns of plasma proteins.
Figure 7B:
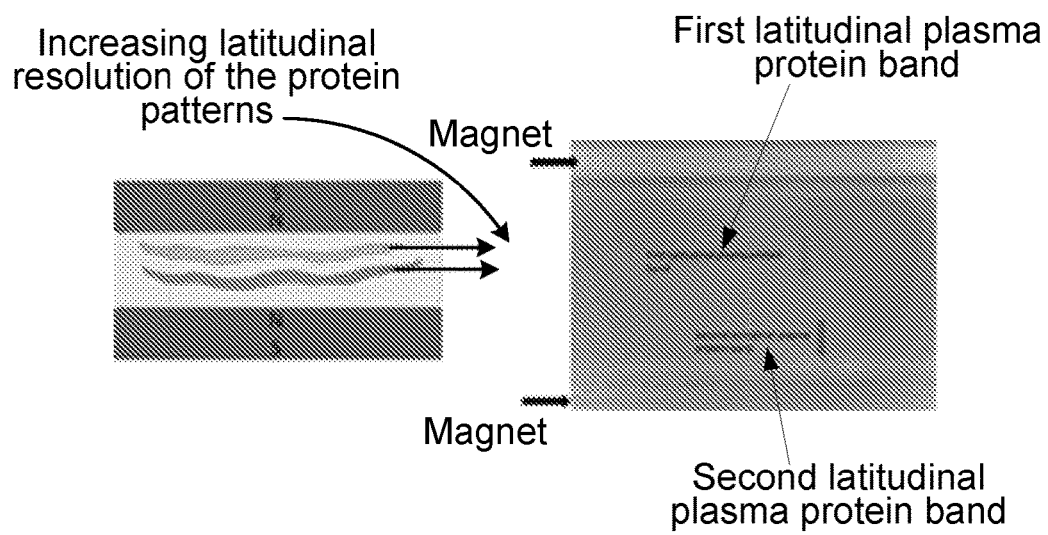
Figure 7C:
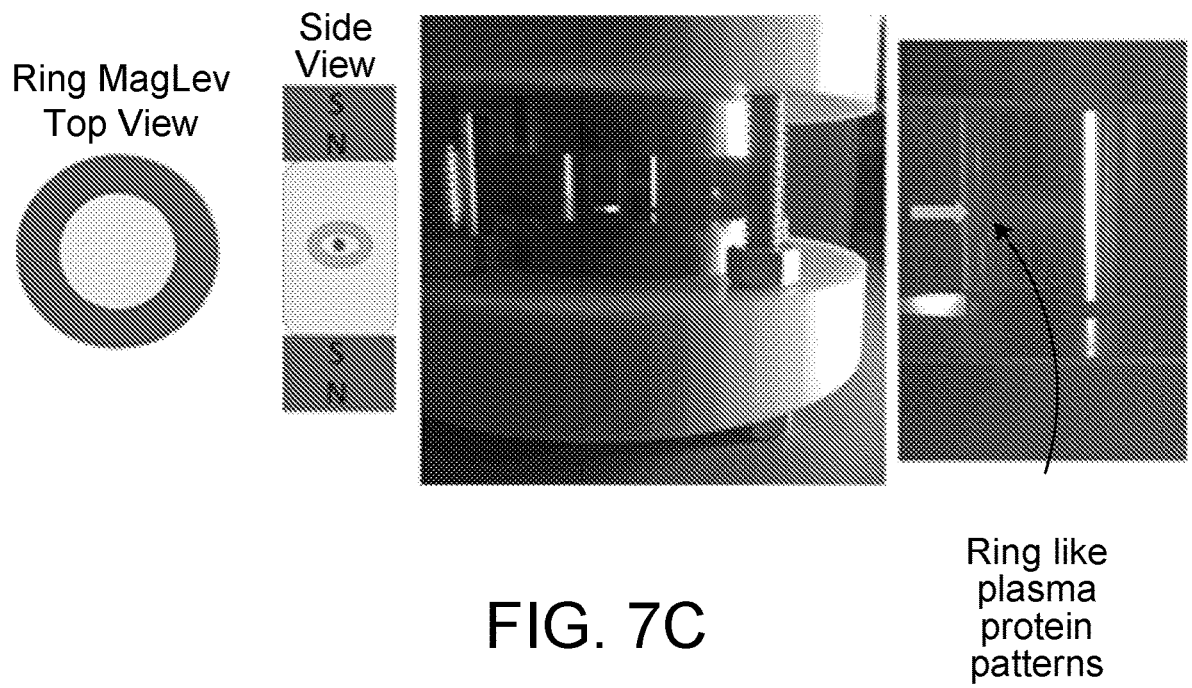
Figure 7D:
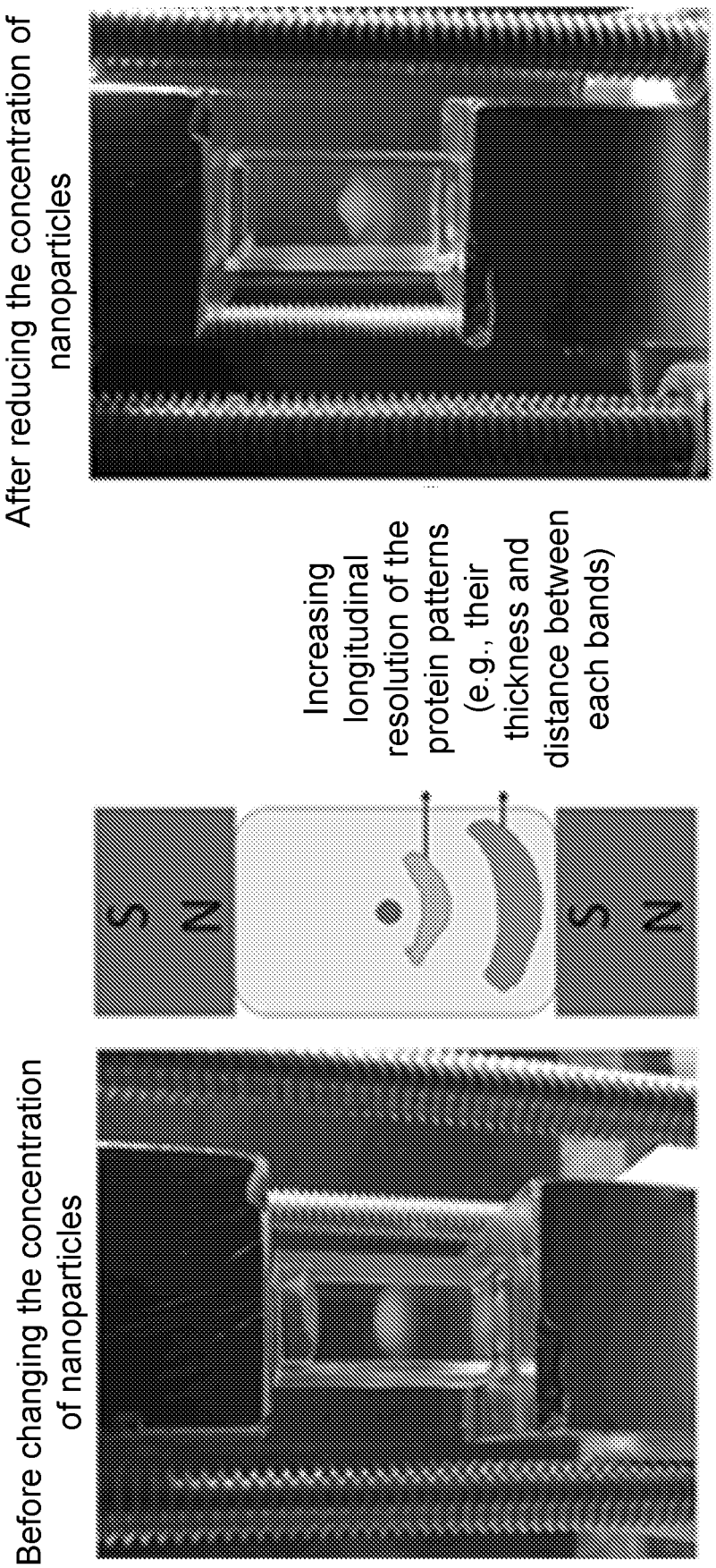
Figure 7E:
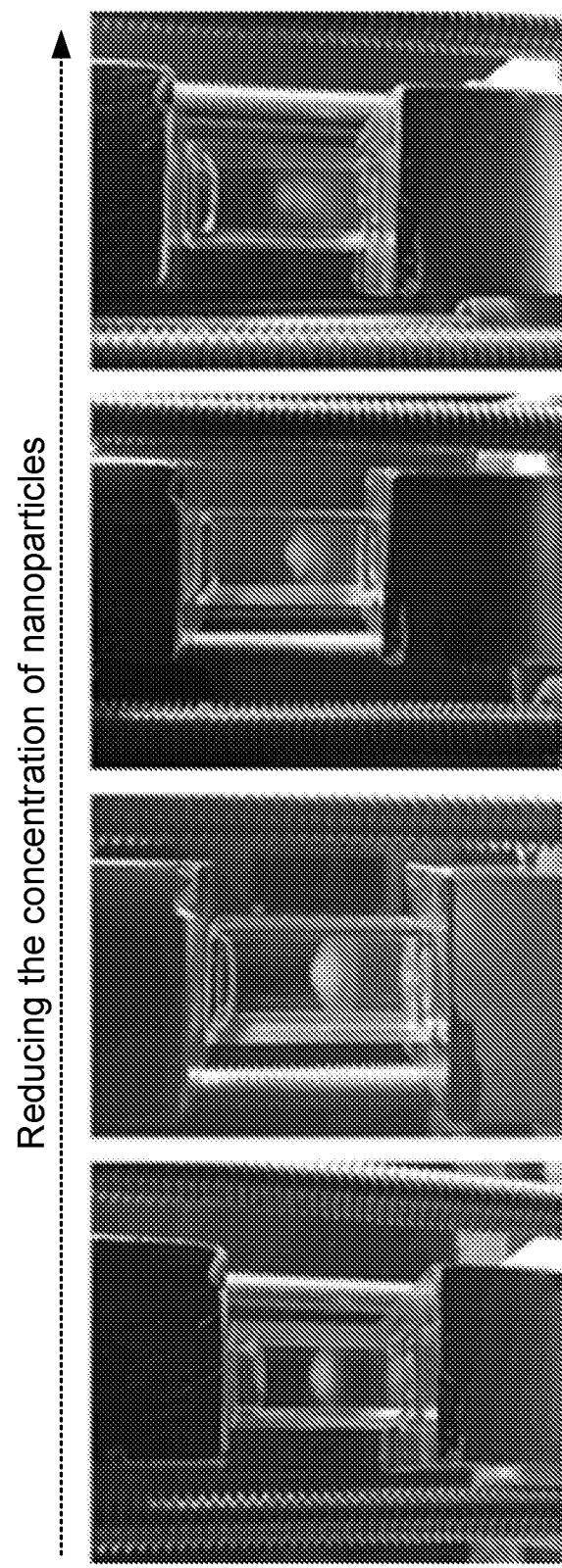

Enhancing the resolution of the MagLev system 100 for the formed protein bands can be achieved by increasing the thickness of the bands and the distance between bands. The increase in thickness of the bands or the distances between the bands can be achieved by, for example, increasing a longitudinal aspect of the MagLev system, adjusting a field strength, or reducing the concentration of SPIONs in the medium. Such enhancement can substantially improve the accuracy of protein (or any types of biomolecule) collection and analysis. In addition, enhancing the resolution of the patterns can be advantageous for the subsequent image-based analysis. FIGS. 7A-E show examples of various aspects of the MagLev system to more advantageously resolve patterns of plasma proteins. In particular, FIG. 7A shows an increase in the longitudinal dimension of the MagLev system to enhance the longitudinal resolution of plasma proteins patterns. FIG. 7B shows an elongated lateral dimension of the magnet poles facing each other in the MagLev system to increase the latitudinal resolution of the protein patterns. FIG. 7C shows a ring configuration of the MagLev system to increase an annular aspect of the levitation process such that the lateral resolution of the protein bands is enhanced by virtue of newly introduced the annular aspect. These examples reinforce earlier discussions associated with FIGS. 3B to G. FIG. 7D shows that an example of changing the concentration of the nanoparticles (e.g., SPIONs, USPIONs) that can increase a longitudinal resolution of the protein patterns by virtue of increased layer thickness and inter-layer separation. FIG. 7E shows another example in which a concentration of SPIONs is reduced to enhance the resolution of the protein plasma band.

Figure 8A:
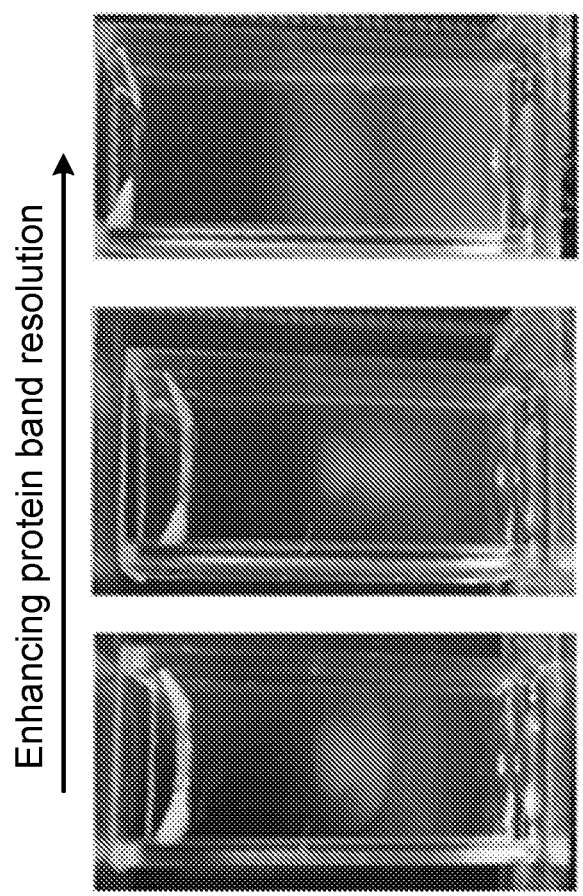

In the case where only one specific protein band is needed for proteomics analysis, this protein band may be levitated by varying the concentration of the superparamagnetic nanoparticles and by subsequently collecting the band using a side cuvette syringe inserted in the MagLev system incorporating, for example, SPIONs in a fluid medium. FIGS. 8A-F show examples of a process of isolating a layer of plasma proteins in the MagLev system. In particular, FIG. 8A shows an example of improving a resolution of layer differentiation when the concentration of the superparamagnetic nanoparticles is gradually reduced. The reduction of nanoparticle concentration is achieved by dilution of the original concentration of nanoparticles. The dilution can be through mixing, for example, phosphate-buffered saline (PBS), with the fluid medium including SPIONs. The range of nanoparticles concentration is from about 0.001 mg/ml to about 30 mg/ml. FIG. 8B shows a syringe needle on the right hand side of a container in which layers of plasma proteins are formed. The syringe has a needle of 29 gauge. The syringe is getting ready to extract contents from the top layer. FIG. 8C to E show various stages of extraction when the syringe needle has entered the container on the right hand side. The size reduction of the top layer indicates successful extraction of contents by the syringe needle. FIG. 8F shows the container with the original top layer extracted when the syringe needle has exited. Thereafter, a liquid chromatography mass spectroscopy (LC-MS/MS) technique, or a gel-electrophoresis technique can be used to analyze the contents from a particular layer. In some cases, a sodium dodecyl sulfate-polyacrylamide gel electrophoresis (SDS-PAGE) analysis of the separated protein patterns can be performed.

Figure 8G:
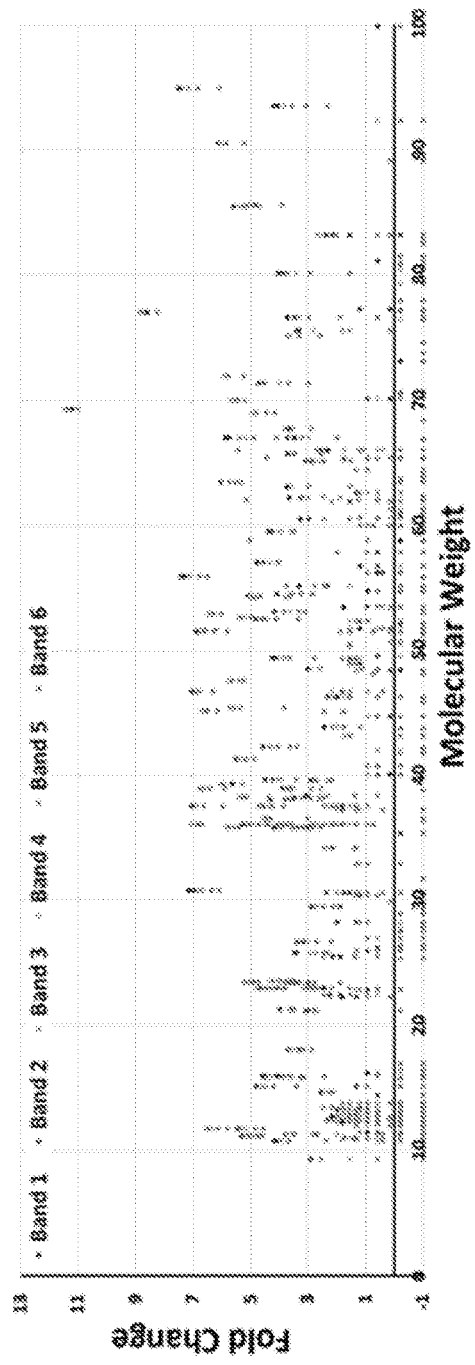
Figure 8H:
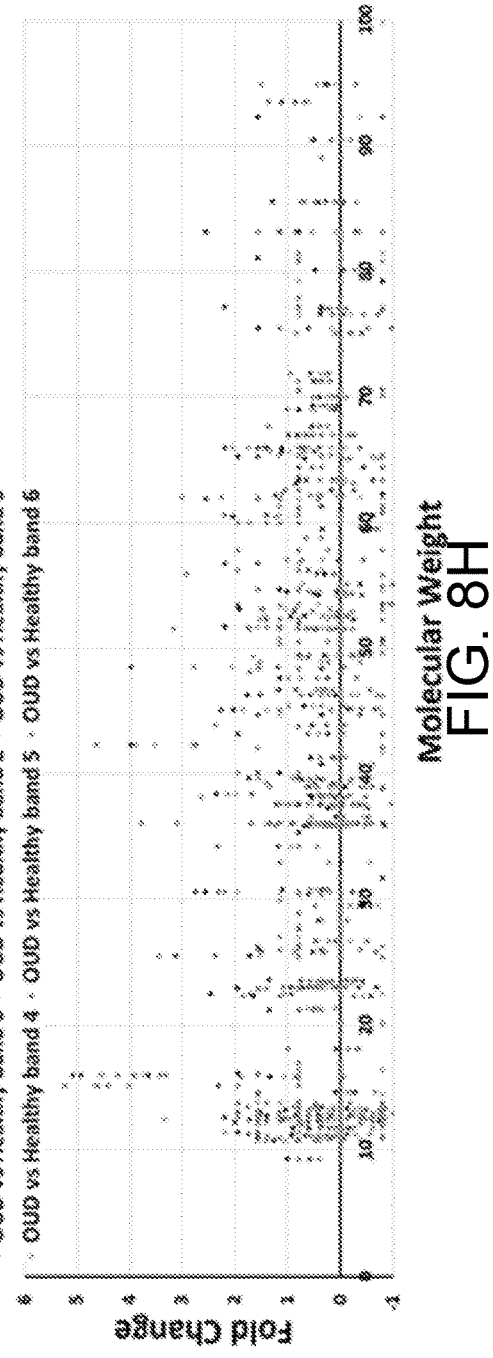

FIG. 8G shows fold change variations of identified protein abundance in different magnetic levitation bands (6 formed bands in total) from healthy individuals, demonstrating the capability of the disclosed MagLev techniques to separate plasma proteins according to their molecular weights and protein-protein interactions. Each dot represents an identified plasma protein. FIG. 8H shows fold change variations of identified protein abundance in different magnetic levitation bands (6 formed bands in total) from opioid use disorder (OUD) patients demonstrating the capacity of the disclosed MagLev technique not only for early detection of disease and also for defining the role of important plasma proteins in disease development. Each dot represents an identified plasma. The different patterns of protein level fold change between healthy individuals and OUD patients confirm the capability of the disclosed MagLev techniques to detect subtle changes in protein/peptide composition, thereby facilitating proteomics to infer protein level quantitation from contents extracted from each layer.

Example 4. MagLev with Optical Resolution

Figure 9:
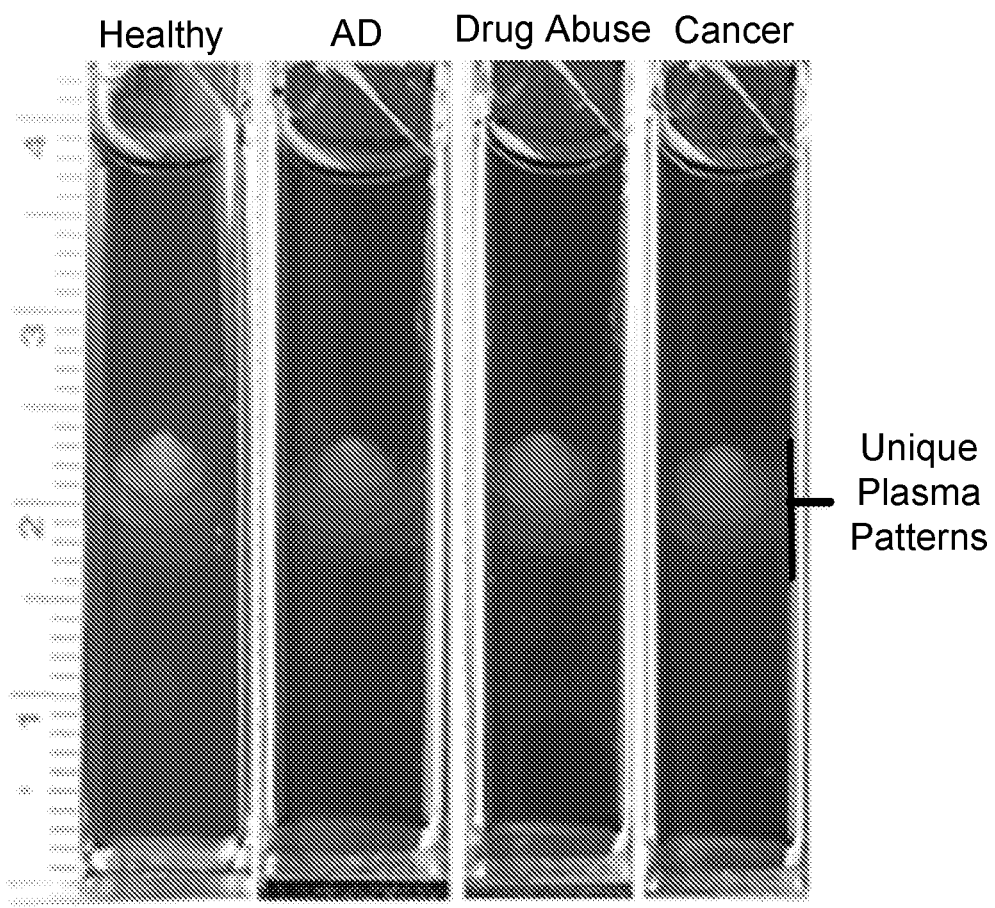
FIG. 9 shows examples of images depicting the formation of distinct human plasma patterns in the MagLev system.

FIG. 9 shows examples of images depicting formation of distinct human plasma patterns profile in the MagLev system. In one illustration, the images can be captured using an optical camera (e.g., Nikon AF-S VR Micro-NIKKOR 105 mm f/2.8G IF-ED Lens). The images reveal formation of reproducible and distinct pattern for each disease. For example, the patterns are different in the healthy individuals, and patients with AD, cancer, and drug abuse disorder. Indeed, plasma macromolecules creates unique patterns in the MagLev system that can be specific to the disease type. Moreover, imaging techniques (e.g., a laser diffraction system in this aim) may introduce additional capacity to identify various stages of AD.

FIGS. 10A-C show examples of an optical system to measure the distinct layers of plasma proteins using laser diffraction patterns. Specifically, FIG. 10A shows laser diffraction system 1000 that includes a laser source 1002, a beam expander 1004, an aperture 1006, a glass tube 1008, a collimator 1010, a lens 1012, a first charge coupled device (CCD) 1014, and a second charge coupled device (CCD) 1016. Laser source 1000 can include a light-emitting diode (LED) source with an output power from 1 mW to 30 mW. The operating wavelength can be from 400 nm to 1300 nm. The bandwidth can be from 0.2 nm to 20 nm. The laser beam passes the beam expander 1004 and the uniform part of the laser beam is selected using an aperture 1006 accordingly. In some cases, the uniform part may correspond to the region where the intensity variation is less than 50%. The aperture 1006 also determines the size of final beam illuminating the plasma protein patterns in the glass tube 1008 of the MagLev system. The MagLev system is placed on a 2-dimensional mechanical micro positioner. A spot with uniform illumination and specific size is generated by the laser beam on the surface of the glass tube 1008 containing the levitated layers of plasma proteins. Through a collimator 1010 and a lens 1012, the resulting light diffraction patterns (e.g., pattern 1009) are collected using charge coupled device (CCD) array 1 (1014) and CCD array 2 (1016). In this illustration, CCD array 1 (1014) and CCD array 2 (1016) can capture the resulting light diffraction patterns from different angles. In some instances, these different angle are substantially orthogonal to acquire the polarized diffraction pattern, which can reveal more orientation information of, for example, plasma macromolecules. The raw CCD images are transferred to a computer for post processing. For example, the raw images can be imported in MATLAB® for image processing. FIG. 10B is a photo showing an example of an actual laser system setup according to FIG. 10A. FIG. 10C shows an example of the formation of diffraction pattern by the MagLev system.

Figure 11A:
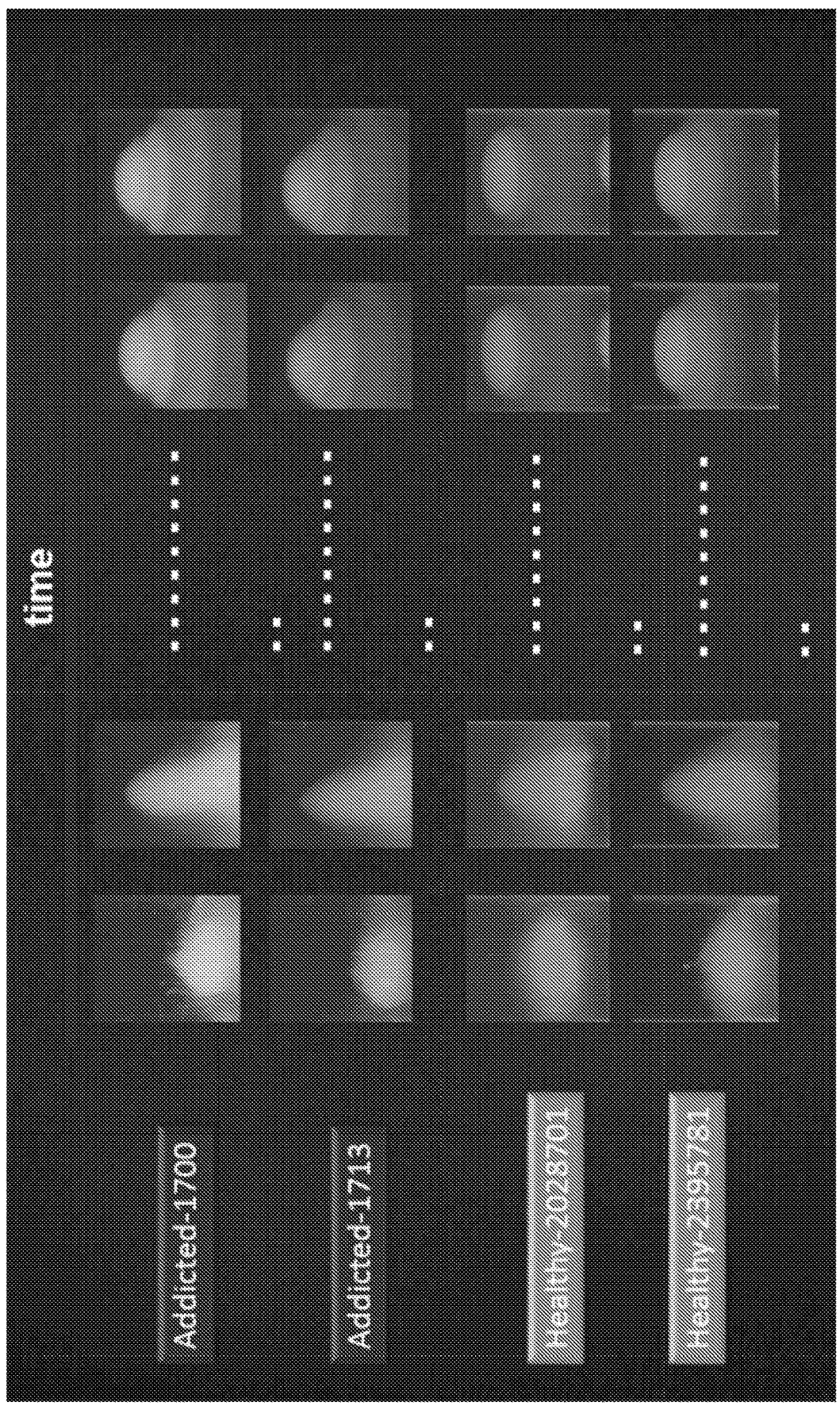
FIGS. 11A-B show examples of images from the MagLev system where profiles of plasma proteins from different groups of subjects are delineated.
Figure 11B:
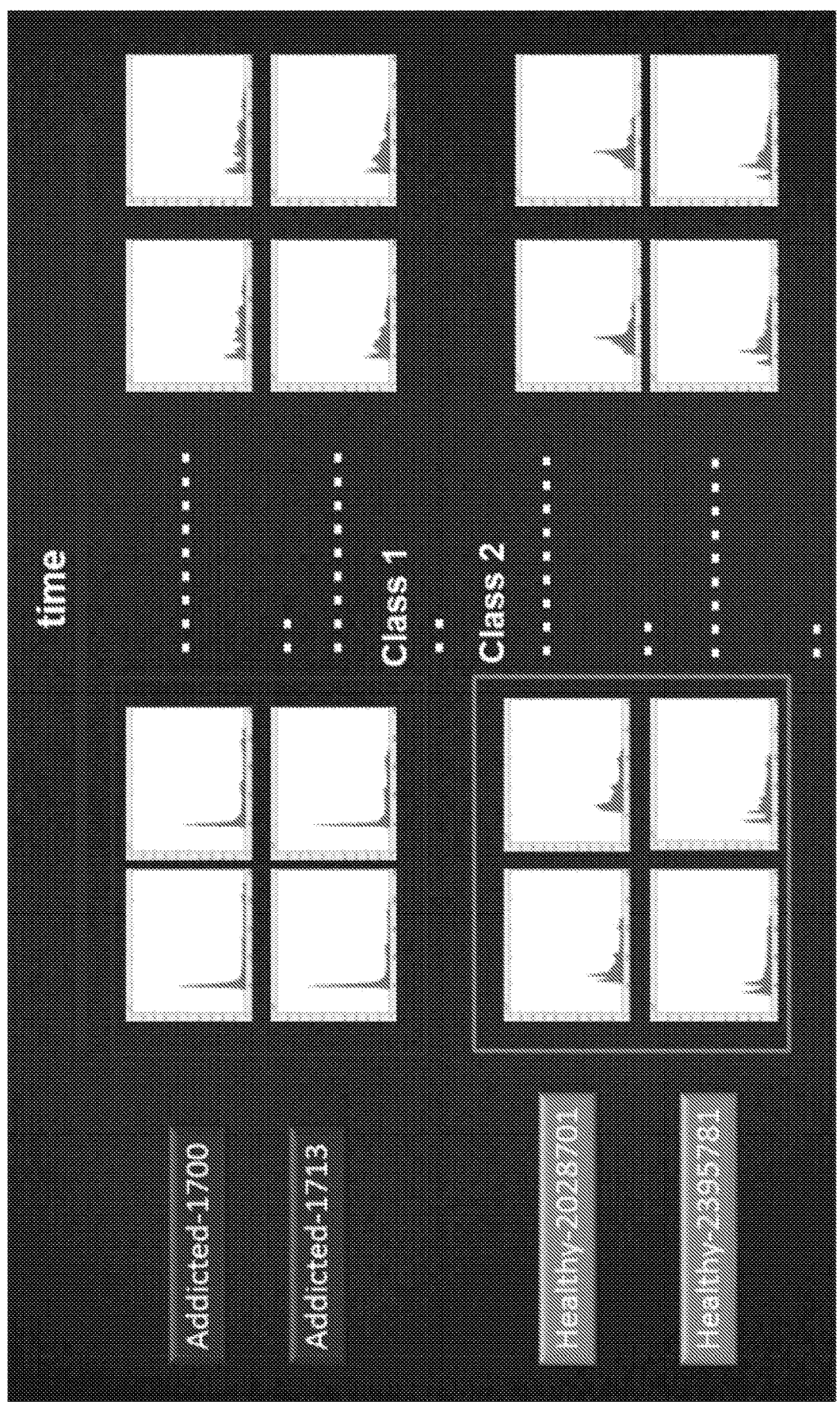

FIGS. 11A-B show examples of images from the MagLev system where profiles of plasma proteins from different groups of subjects are delineated. In particular, FIG. 11A shows the profiles of plasma proteins from a first group of two addicted patients (addicted group) and a second group of two healthy individuals (control group). The addicted group in this example is addicted to methadone. While the profiles from the addicted group and the control group appear similar (other than brightness) during the earlier period on the MagLev system, after settling for sufficient time (e.g., more than 10 minutes), the two groups demonstrate marked difference in the profiles. The timescale of settling can range from ten seconds to ten hours. This time scale may relate to the concentration of the nanoparticles. The profile for the addicted group resembles a sector chart. The profile for the control group, on the other hand, appears more oval in shape. FIG. 11B shows the corresponding histograms of the addicted group and the control group. As indicated, during the initial period on the MagLev system, the addicted group show much higher counts of proteins at specific heights than the control group. As the samples settle (e.g., after hours), the addicted group now has more uniform distribution of the proteins at various heights than the control group. As such, the MagLev system can successfully perform classification: differentiating a first group of addicted patients and a second group of health individuals.

Example 5. MagLev for Quality Control

Figure 12:
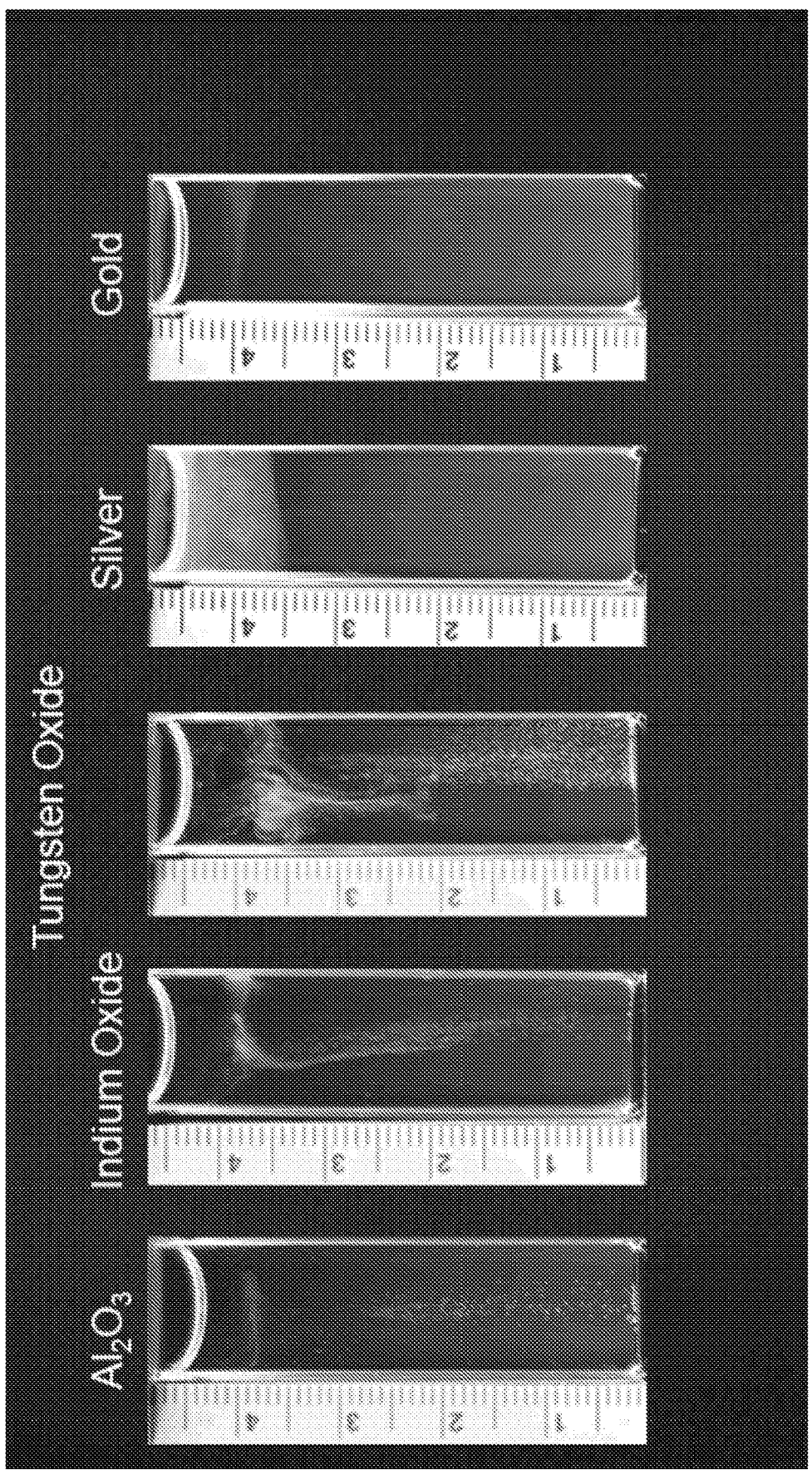
FIG. 12 show examples of images from the MagLev system where profiles of various nanoparticles are delineated for quality control.

FIG. 12 show examples of images from the MagLev system where profiles of various nanoparticles are delineated for quality control. Various nanoparticles including aluminum oxide ($Al_2O_3$), indium oxide, tungsten oxide, silver, and gold are analyzed on the MagLev system. As demonstrated, all five groups demonstrates specific levitation patterns. For silver and gold, the levitated patterns are generally concentrated towards one end of the glass tube (towards one of the opposing poles). For aluminum oxide, indium oxide, tungsten oxide, the levitated patterns are more evenly distributed along the height dimension. Therefore, the MagLev system described in this disclosure is capable of levitating not only biomolecules but also nanoparticles. Such biomolecules and nanoparticles may be jointly referred to as molecular entities.

REFERENCES

1. Keshishian H, Burgess M W, Specht H, Wallace L, Clauser K R, Gillette M A, et al. Quantitative, multiplexed workflow for deep analysis of human blood plasma and biomarker discovery by mass spectrometry. *nature protocols* 2017, 12(8): 1683.
2. Etzioni R, Urban N, Ramsey S, McIntosh M, Schwartz S, Reid B, et al. The case for early detection. *Nature Reviews Cancer* 2003, 3(4): 243-252.
3. Cuzick J, Thorat M A, Andriole G, Brawley O W, Brown P H, Culig Z, et al. Prevention and early detection of prostate cancer. *The Lancet Oncology*, 15(11): e484-e492.
4. Mirica K A, Shevkoplyas S S, Phillips S T, Gupta M, Whitesides G M. Measuring densities of solids and liquids using magnetic levitation: fundamentals. *Journal of the American Chemical Society* 2009, 131(29): 10049-10058.
5. Bwambok D K, Thuo M M, Atkinson M B, Mirica K A, Shapiro N D, Whitesides G M. Paramagnetic ionic liquids for measurements of density using magnetic levitation. *Analytical chemistry* 2013, 85(17): 8442-8447.
6. Shapiro N D, Soh S, Mirica K A, Whitesides G M. Magnetic levitation as a platform for competitive protein—ligand binding assays. *Analytical chemistry* 2012, 84(14): 6166-6172.
7. Lockett M R, Mirica K A, Mace C R, Blackledge R D, Whitesides G M. Analyzing forensic evidence based on density with magnetic levitation. *Journal of forensic sciences* 2013, 58(1): 40-45.
8. Durmus N G, Tekin H C, Guven S, Sridhar K, Yildiz A A, Calibasi G, et al. Magnetic levitation of single cells. *Proceedings of the National Academy of Sciences* 2015, 112(28): E3661-E3668.
9. Turker E, Arslan-Yildiz A. Recent Advances in Magnetic Levitation: A Biological Approach from Diagnostics to Tissue Engineering. *ACS Biomaterials Science & Engineering* 2018, 4(3): 787-799.
10. Hirschbein B L, Brown D W, Whitesides G M. Magnetic separations in chemistry and biochemistry. *Chemtech* 1982, 12(3): 172-179.
11. Thomas T E, Abraham S J, Otter A J, Blackmore E W, Lansdorp P M. High gradient magnetic separation of cells on the basis of expression levels of cell surface antigens. *Journal of immunological methods* 1992, 154(2): 245-252.
12. Weber C, Falkenhagen D. Specific blood purification by means of antibody-conjugated magnetic microspheres. *Scientific and Clinical Applications of Magnetic Carriers*. Springer, 1997, pp 371-378.
13. Whitesides G M, Kazlauskas R J, Josephson L. Magnetic separations in biotechnology. *Trends in Biotechnology* 1983, 1(5): 144-148.
14. Zhao W, Cheng R, Miller J R, Mao L. Label-Free Microfluidic Manipulation of Particles and Cells in Magnetic Liquids. *Advanced Functional Materials* 2016, 26(22): 3916-3932.
15. Kose A R, Koser H. Ferrofluid mediated nanocytometry. *Lab on a Chip* 2012, 12(1): 190-196.
16. Kostic A D, Gevers D, Siljander H, Vatanen T, Hyotylainen T, Hamalainen A M, et al. The dynamics of the human infant gut microbiome in development and in progression toward type 1 diabetes. *Cell Host Microbe* 2015, 17(2): 260-273.
17. Zhao W, Zhu T, Cheng R, Liu Y, He J, Qiu H, et al. Label-Free and Continuous-Flow Ferrohydrodynamic Separation of HeLa Cells and Blood Cells in Biocompatible Ferrofluids. *Advanced functional materials* 2015.
18. Mahmoudi M, Sant S, Wang B, Laurent S, Sen T. Superparamagnetic iron oxide nanoparticles (SPIONs): development, surface modification and applications in chemotherapy. *Advanced drug delivery reviews* 2011, 63(1-2): 24-46.
19. Mahmoudi M, Simchi A, Imani M, Milani A S, Stroeve P. Optimal design and characterization of superparamagnetic iron oxide nanoparticles coated with polyvinyl alcohol for targeted delivery and imaging. *The Journal of Physical Chemistry B* 2008, 112(46): 14470-14481.
20. Laurent S, Dutz S, Hafeli U O, Mahmoudi M. Magnetic fluid hyperthermia: focus on superparamagnetic iron oxide nanoparticles. *Advances in colloid and interface science* 2011, 166(1-2): 8-23.
21. Mahmoudi M, Hofmann H, Rothen-Rutishauser B, Petri-Fink A. Assessing the in vitro and in vivo toxicity of superparamagnetic iron oxide nanoparticles. *Chemical reviews* 2011, 112(4): 2323-2338.
22. Mahmoudi M, Simchi A, Milani A, Stroeve P. Cell toxicity of superparamagnetic iron oxide nanoparticles. *Journal of colloid and interface science* 2009, 336(2): 510-518.
23. Mahmoudi M, Simchi A, Imani M, Hafeli U O. Superparamagnetic iron oxide nanoparticles with rigid cross-linked polyethylene glycol fumarate coating for application in imaging and drug delivery. *The Journal of Physical Chemistry C* 2009, 113(19): 8124-8131.
24. Mahmoudi M, Shokrgozar M A, Sardari S, Moghadam M K, Vali H, Laurent S, et al. Irreversible changes in protein conformation due to interaction with superparamagnetic iron oxide nanoparticles. *Nanoscale* 2011, 3(3): 1127-1138.
25. Sakulkhu U, Mahmoudi M, Maurizi L, Salaklang J, Hofmann H. Protein corona composition of superparamagnetic iron oxide nanoparticles with various physicochemical properties and coatings. *Scientific reports* 2014, 4: 5020.
26. Amiri H, Bordonali L, Lascialfari A, Wan S, Monopoli M P, Lynch I, et al. Protein corona affects the relaxivity and MRI contrast efficiency of magnetic nanoparticles. *Nanoscale* 2013, 5(18): 8656-8665.
27. Sharifi S, Seyednejad H, Laurent S, Atyabi F, Saei A A, Mahmoudi M. Superparamagnetic iron oxide nanoparticles for in vivo molecular and cellular imaging. *Contrast media & molecular imaging* 2015, 10(5): 329-355.
28. Sasanpour P, Dilmaghani-Marand A, Montazeri H, Ivani S, Hajipour M J, Mahmoudi M. Nanoparticles affect bacterial colonies' optical diffraction patterns. *Nanoscale* 2019.
29. Badieyan S, Dilmaghani-Marand A, Hajipour M J, Amen A, Razzaghi M R, Rafii-Tabar H, et al. Detection and discrimination of bacterial colonies with Mueller matrix imaging. *Scientific reports* 2018, 8(1): 10815.
30. Carter H B, Albertsen P C, Barry M J, Etzioni R, Freedland S J, Greene K L, et al. Early detection of prostate cancer: AUA Guideline. *The Journal of urology* 2013, 190(2): 419-426.
31. Levin B, Lieberman D A, McFarland B, Smith R A, Brooks D, Andrews K S, et al. Screening and surveillance for the early detection of colorectal cancer and adenomatous polyps, 2008: a joint guideline from the American Cancer Society, the U S Multi-Society Task Force on Colorectal Cancer, and the American College of Radiology*†. *CA: a cancer journal for clinicians* 2008, 58(3): 130-160.
32. Wulfkuhle J D, Liotta L A, Petricoin E F. Proteomic applications for the early detection of cancer. *Nature reviews cancer* 2003, 3(4): 267-275.
33. Hirsch F R, Franklin W A, Gazdar A F, Bunn P A. Early detection of lung cancer: clinical perspectives of recent advances in biology and radiology. *Clinical Cancer Research* 2001, 7(1): 5-22.
34. Baird A L, Westwood S, Lovestone S. Blood-based proteomic biomarkers of Alzheimer's disease pathology. *Frontiers in neurology* 2015, 6: 236.
35. Liu Y, Qing H, Deng Y. Biomarkers in Alzheimer's disease analysis by mass spectrometry-based proteomics. *International journal of molecular sciences* 2014, 15(5): 7865-7882.
36. Pepe M S, Etzioni R, Feng Z, Potter J D, Thompson M L, Thornquist M, et al. Phases of biomarker development for early detection of cancer. *Journal of the National Cancer Institute* 2001, 93(14): 1054-1061.
37. Smith R A, Cokkinides V, von Eschenbach A C, Levin B, Cohen C, Runowicz C D, et al. American Cancer Society guidelines for the early detection of cancer. *CA: a cancer journal for clinicians* 2002, 52(1): 8-22.
38. Petricoin E F, Liotta L A. SELDI-TOF-based serum proteomic pattern diagnostics for early detection of cancer. *Current Opinion in Biotechnology* 2004, 15(1): 24-30.
39. Henschke C I, McCauley D I, Yankelevitz D F, Naidich D P, McGuinness G, Miettinen O S, et al. Early Lung Cancer Action Project: overall design and findings from baseline screening. *The Lancet* 1999, 354(9173): 99-105.
40. Guo L-H, Alexopoulos P, Wagenpfeil S, Kurz A, Perneczky R, Initiative AsDN. Plasma proteomics for the identification of Alzheimer's disease. *Alzheimer disease and associated disorders* 2013, 27(4).
41. Hye A, Lynham S, Thambisetty M, Causevic M, Campbell J, Byers H, et al. Proteome-based plasma biomarkers for Alzheimer's disease. *Brain* 2006, 129(11): 3042-3050.
42. Fontana R S, Sanderson D R, Taylor W F, Woolner L B, Miller W E, Muhm J R, et al. Early Lung Cancer Detection: Results of the Initial (Prevalence) Radiologic and Cytologic Screening in the Mayo Clinic Study 1, 2. *American Review of Respiratory Disease* 1984, 130(4): 561-565.
43. Hajipour M J, Santoso M R, Rezaee F, Aghaverdi H, Mahmoudi M, Perry G. Advances in Alzheimer's diagnosis and therapy: the implications of nanotechnology. *Trends in biotechnology* 2017, 35(10): 937-953.
44. Ferrari M. Cancer nanotechnology: opportunities and challenges. *Nature Reviews Cancer* 2005, 5(3): 161-171.
45. Shi J, Kantoff P W, Wooster R, Farokhzad O C. Cancer nanomedicine: progress, challenges and opportunities. *Nature Reviews Cancer* 2017, 17(1): 20.
46. Zheng G, Patolsky F, Cui Y, Wang W U, Lieber C M. Multiplexed electrical detection of cancer markers with nanowire sensor arrays. *Nature biotechnology* 2005, 23(10): 1294-1301.
47. Hajipour M J, Ghasemi F, Aghaverdi H, Raoufi M, Linne U, Atyabi F, et al. Sensing of Alzheimer's Disease and Multiple Sclerosis Using Nano-Bio Interfaces. *Journal of Alzheimer's Disease* 2017, 59(4): 1187-1202.
48. Tan H T, Low J, Lim S G, Chung M. Serum autoantibodies as biomarkers for early cancer detection. *FEBS journal* 2009, 276(23): 6880-6904.
49. Hanash S M, Pitteri S J, Faca V M. Mining the plasma proteome for cancer biomarkers. *Nature* 2008, 452(7187): 571-579.
50. Salvador-Morales C, Zhang L, Langer R, Farokhzad O C. Immunocompatibility properties of lipid-polymer hybrid nanoparticles with heterogeneous surface functional groups. *Biomaterials* 2009, 30(12): 2231-2240.
51. Monopoli M P, Aberg C, Salvati A, Dawson K A. Biomolecular coronas provide the biological identity of nanosized materials. *Nature nanotechnology* 2012, 7(12): 779.
52. Hajipour M J, Laurent S, Aghaie A, Rezaee F, Mahmoudi M. Personalized protein coronas: a "key" factor at the nanobiointerface. *Biomaterials Science* 2014, 2(9): 1210-1221.
53. Hajipour M J, Raheb J, Akhavan O, Arjmand S, Mashinchian O, Rahman M, et al. Personalized disease-specific protein corona influences the therapeutic impact of graphene oxide. *Nanoscale* 2015, 7(19): 8978-8994.
54. Rahman M, Mahmoudi M. Disease specific protein corona. *SPIE* BiOS; 2015: International Society for Optics and Photonics; 2015. p. 93380V-93380V-93388.
55. Mahmoudi M, Laurent S, Stroeve P. *Protein-Nanoparticle Interactions: The Bio-Nano Interface*. Springer Berlin, 2013.
56. Mahmoudi M, Abdelmonem A M, Behzadi S, Clement J H, Dutz S, Ejtehadi M R, et al. Temperature: the "ignored" factor at the nanobio interface. *ACS nano* 2013, 7(8): 6555-6562.
57. Mirshafiee V, Kim R, Park S, Mahmoudi M, Kraft M L. Impact of protein pre-coating on the protein corona composition and nanoparticle cellular uptake. *Biomaterials* 2016, 75: 295-304.
58. Mahmoudi M, Lohse S E, Murphy C J, Fathizadeh A, Montazeri A, Suslick K S. Variation of protein corona composition of gold nanoparticles following plasmonic heating. *Nano letters* 2013, 14(1): 6-12.
59. Bertrand N, Grenier P, Mahmoudi M, Lima E M, Appel E A, Dormont F, et al. Mechanistic understanding of in vivo protein corona formation on polymeric nanoparticles and impact on pharmacokinetics. *Nature communications* 2017, 8(1): 777.
60. Caracciolo G, Farokhzad O C, Mahmoudi M. Biological identity of nanoparticles in vivo: clinical implications of the protein corona. *Trends in biotechnology* 2017, 35(3): 257-264.
61. Saha K, Rahimi M, Yazdani M, Kim S T, Moyano D F, Hou S, et al. Regulation of macrophage recognition through the interplay of nanoparticle surface functionality and protein corona. *ACS nano* 2016, 10(4): 4421-4430.
62. Bigdeli A, Palchetti S, Pozzi D, Hormozi-Nezhad M R, Baldelli Bombelli F, Caracciolo G, et al. Exploring cellular interactions of liposomes using protein corona fingerprints and physicochemical properties. *ACS nano* 2016, 10(3): 3723-3737.
63. Mahmoudi M, Bertrand N, Zope H, Farokhzad O C. Emerging understanding of the protein corona at the nano-bio interfaces. *Nano Today* 2016, 11(6): 817-832.
64. Mahmoudi M. Antibody orientation determines corona mistargeting capability. *Nature nanotechnology* 2018, 13: 775-776.
65. Serpooshan V, Sheibani S, Pushparaj P, Wojcik M, Jang A Y, Santoso M R, et al. Effect of Cell Sex on Uptake of Nanoparticles: The Overlooked Factor at the Nanobio Interface. *ACS nano* 2018, 12(3): 2253-2266.
66. Quillin M L, Matthews B W. Accurate calculation of the density of proteins. *Acta Crystallographica Section D: Biological Crystallography* 2000, 56(7): 791-794.
67. Fischer H, Polikarpov I, Craievich A F. Average protein density is a molecular-weight-dependent function. *Protein Science* 2004, 13(10): 2825-2828.
68. Kantardjieff K A, Rupp B. Matthews coefficient probabilities: improved estimates for unit cell contents of proteins, DNA, and protein—nucleic acid complex crystals. *Protein Science* 2003, 12(9): 1865-1871.
69. Mirica K A, Ilievski F, Ellerbee A K, Shevkoplyas S S, Whitesides G M. Using Magnetic Levitation for Three Dimensional Self-Assembly. *Advanced Materials* 2011, 23(36): 4134-4140.
70. Koscielny G, An P, Carvalho-Silva D, Cham J A, Fumis L, Gasparyan R, et al. Open Targets: a platform for therapeutic target identification and validation. *Nucleic acids research* 2016, 45(D1): D985-D994.
71. Welter D, MacArthur J, Morales J, Burdett T, Hall P, Junkins H, et al. The NHGRI GWAS Catalog, a curated resource of SNP-trait associations. *Nucleic acids research* 2013, 42(D1): D1001-D1006.
72. Consortium U. UniProt: a hub for protein information. *Nucleic acids research* 2014: gku989.
73. Wright C F, Fitzgerald T W, Jones W D, Clayton S, McRae J F, Van Kogelenberg M, et al. Genetic diagnosis of developmental disorders in the DDD study: a scalable analysis of genome-wide research data. *The Lancet* 2015, 385(9975): 1305-1314.
74. Forbes S A, Beare D, Gunasekaran P, Leung K, Bindal N, Boutselakis H, et al. COSMIC: exploring the world's knowledge of somatic mutations in human cancer. *Nucleic acids research* 2014, 43(D1): D805-D811.
75. Rubio-Perez C, Tamborero D, Schroeder M P, Antolin A A, Deu-Pons J, Perez-Llamas C, et al. In silico prescription of anticancer drugs to cohorts of 28 tumor types reveals targeting opportunities. *Cancer cell* 2015, 27(3): 382-396.
76. Consortium E P. Europe PMC: a full-text literature database for the life sciences and platform for innovation. *Nucleic acids research* 2014: gku1061.
77. Croft D, Mundo A F, Haw R, Milacic M, Weiser J, Wu G, et al. The Reactome pathway knowledgebase. *Nucleic acids research* 2013, 42(D1): D472-D477.
78. Esteva A, Kuprel B, Novoa R A, Ko J, Swetter S M, Blau H M, et al. Dermatologist-level classification of skin cancer with deep neural networks. *Nature* 2017, 542 (7639): 115.
79. Askim J R, Mahmoudi M, Suslick K S. Optical sensor arrays for chemical sensing: the optoelectronic nose. *Chemical Society Reviews* 2013, 42(22): 8649-8682.
80. Lim S H, Feng L, Kemling J W, Musto C J, Suslick K S. An optoelectronic nose for the detection of toxic gases. *Nature chemistry* 2009, 1(7): 562-567.
81. Suslick B A, Feng L, Suslick K S. Discrimination of complex mixtures by a colorimetric sensor array: coffee aromas. *Analytical chemistry* 2010, 82(5): 2067-2073.
82. Carey J R, Suslick K S, Hulkower K I, Imlay J A, Imlay K R, Ingison C K, et al. Rapid identification of bacteria with a disposable colorimetric sensing array. *Journal of the American Chemical Society* 2011, 133(19): 7571-7576.
83. Zhang Y, Askim J R, Zhong W, Orlean P, Suslick K S. Identification of pathogenic fungi with an optoelectronic nose. *Analyst* 2014, 139(8): 1922-1928.
84. Ghasemi F, Hormozi-Nezhad M R, Mahmoudi M. Identification of catecholamine neurotransmitters using fluorescence sensor array. *Analytica Chimica Acta* 2016, 917: 85-92.
85. Mahmoudi M, Lohse S, Murphy C J, Suslick K S. Identification of Nanoparticles with a Colorimetric Sensor Array. *ACS Sensors* 2016, 1(1): 17-21.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for separating a plurality of sub-micron sized plasma molecular entities with differing densities, the system comprising:
    a pair of magnetic poles of like polarity to provide a magnetic field; and
    a container holding the plurality of sub-micron sized plasma molecular entities in a fluid medium comprising superparamagnetic nanoparticles that substantially change a magnetic susceptibility of the fluid medium while preserving a stability of the sub-micron sized plasma molecular entities such that, when the container is placed inside the magnetic field, sufficient gradients in an effective density of the fluid medium are generated inside the container to levitate the plurality of sub-micron sized plasma molecular entities, with the preserved stability, to respective layers within the container, each respective layer corresponding to a respective density.

2. The system of claim 1, wherein the superparamagnetic nanoparticles comprise at least one of: superparamagnetic iron oxide nanoparticles (SPIO), monocrystalline iron oxide nanoparticles (MIONs), Ultrasmall Superparamagnetic Iron Oxides (USPIOs), or a type of ferromagnetic or ferrimagnetic nanoparticles.

3. The system of claim 2, wherein the type of ferromagnetic or ferrimagnetic nanoparticles include at least one of: a yttrium iron garnet, a cubic ferrite; and a hexagonal ferrite.

4. The system of claim 1, wherein the fluid medium includes at least one of: a superparamagnetic nanoparticle ferrofluid, a ferromagnetic nanoparticle ferrofluid, or a ferrimagnetic nanoparticle ferrofluid.

5. The system of claim 1, wherein the superparamagnetic nanoparticles are not attached or bound to at least portions of the plurality of sub-micron sized plasma molecular entities.

6. The system of claim 1, wherein the superparamagnetic nanoparticles are attached or bound to at least portions of the plurality of sub-micron sized plasma molecular entities.

7. The system of claim 1, wherein a concentration of the superparamagnetic nanoparticles in the fluid medium is about 0.001 mg/ml to about 30 mg/ml.

8. The system of claim 1, wherein the pair of magnetic poles are separated by a distance accommodating the container, wherein the distance is about 0.005 cm to 50 cm, and wherein the magnetic field is about 0.002 Tesla to 10 Tesla.

9. The system of claim 1, wherein the container comprises a port to allow extraction of at least portions of a respective layer of the plurality of sub-micron sized plasma molecular entities from the container.

10. The system of claim 1, further comprising an imaging system comprising one or more camera devices configured to perform image-based detection of the plurality of sub-micron sized plasma molecular entities levitated to the respective layers within the container.

11. The system of claim 1, further comprising a laser system that includes:
a laser source configured to generate a laser beam;
passive optical components configured to guide the laser beam to irradiate the container; and
one or more detectors configured to record an optical signal from the respective layers in response to being irradiated by the laser beam,
wherein the laser source includes a laser diode configured to output an optical power between 1 mW and 30 mW with an optical wavelength between 400 nm and 1300 nm,
wherein the passive optical components include at least one of: a beam expander, an aperture, a grating, or a fiber, and
wherein the one or more detectors include at least one charge-coupled device (CCD).

12. A method for separating a plurality of sub-micron sized plasma molecular entities with differing densities, the method comprising:
introducing the plurality of sub-micron sized plasma molecular entities into a fluid medium comprising superparamagnetic nanoparticles that substantially change a magnetic susceptibility of the fluid medium while preserving a stability of the sub-micron sized plasma molecular entities; and
subsequently placing the fluid medium in a magnetic field to generate sufficient gradients in an effective density of the fluid medium inside a container such that the plurality of sub-micron sized plasma molecular entities, with the preserved stability, are levitated to respective layers inside the container, each respective layer corresponding to a respective density.

13. The method of claim 12, further comprising:
extracting at least a portion of a respective layer comprising at least one of the plurality of sub-micron sized plasma molecular entities; and
analyzing the portion of the respective layer using a technique for proteomics, lipidomics, or metabolomics, wherein the technique for proteomics, lipidomics, or metabolomics comprises at least one of: a liquid chromatography mass spectroscopy (LC-MS/MS) technique, or a gel-electrophoresis technique.

14. The method of claim 12, further comprising:
adjusting a concentration of the superparamagnetic nanoparticles in the fluid medium to change a separation of the respective layers, wherein the concentration vary from about 0.001 mg/ml to about 30 mg/ml, wherein the nanoparticles comprise at least one of: superparamagnetic iron oxide nanoparticles (SPIO), Ultrasmall Superparamagnetic Iron Oxides (USPIOs), or a type of ferromagnetic or ferrimagnetic nanoparticles,
wherein the type of ferromagnetic or ferrimagnetic nanoparticles includes at least one of: a yttrium iron garnet, a cubic ferrite, and a hexagonal ferrite, and
wherein the fluid medium includes at least one of: a superparamagnetic nanoparticle ferrofluid, a ferromagnetic nanoparticle ferrofluid, or a ferrimagnetic nanoparticle ferrofluid.

15. The method of claim 14, wherein the superparamagnetic nanoparticles are not attached to at least portions of the plurality of sub-micron sized plasma molecular entities.

16. The method of claim 14, wherein the superparamagnetic nanoparticles are attached or bound to at least portions of the plurality of sub-micron sized plasma molecular entities.

17. The method of claim 12, further comprising:
optically resolving the respective layers of the plurality of sub-micron sized plasma molecular entities to perform image-based detection of the plurality of sub-micron sized plasma molecular entities levitated to the respective layers.

18. The method of claim 17, wherein placing the fluid medium in the magnetic field occurs at a first time point, wherein optically resolving the respective layers of the plurality of sub-micron sized plasma molecular entities occurs at a second time point, and wherein the first time point precedes the second time point by about 10 seconds to 10 hours.

19. The method of claim 17, wherein optically resolving comprises:
energizing a laser source to generate a laser beam;
irradiating each of the respective layers with the laser beam; and
recording an optical signal from each of the respective layers in response to being irradiated by the laser beam, wherein the laser beam is characterized as having an optical power between 1 mW and 30 mW and an optical wavelength between 400 nm and 1300 nm.

20. The method of claim 12, wherein the magnetic field is characterized as having a field strength of about 0.002 Tesla to 10 Tesla.

* * * * *